(12) United States Patent
Horton, III

(10) Patent No.: US 6,403,030 B1
(45) Date of Patent: *Jun. 11, 2002

(54) ULTRAVIOLET WASTEWATER DISINFECTION SYSTEM AND METHOD

(76) Inventor: Isaac B. Horton, III, 8824 Stage Ford Rd., Raleigh, NC (US) 27615

( * ) Notice: Subject to any disclaimer, the term of this patent is extended or adjusted under 35 U.S.C. 154(b) by 0 days.

This patent is subject to a terminal disclaimer.

(21) Appl. No.: 09/723,733

(22) Filed: Nov. 28, 2000

Related U.S. Application Data

(63) Continuation-in-part of application No. 09/630,245, filed on Jul. 31, 2000.

(51) Int. Cl.⁷ .................................................. A61L 2/00
(52) U.S. Cl. ...................... 422/24; 250/450.11; 210/748
(58) Field of Search ........................ 422/24; 250/450.11; 210/748

(56) References Cited

U.S. PATENT DOCUMENTS

| | | | |
|---|---|---|---|
| 4,008,045 A | * | 2/1977 | Free |
| 5,501,801 A | * | 3/1996 | Zhang et al. ............... 210/748 |
| 5,751,870 A | * | 5/1998 | Forkner et al. .............. 385/33 |
| 5,780,860 A | | 7/1998 | Gadgil et al. |
| 5,857,041 A | * | 1/1999 | Riser et al. ................... 385/31 |
| 5,911,020 A | * | 6/1999 | Riser et al. ................... 385/33 |
| 5,992,684 A | | 11/1999 | Russell |
| 6,027,766 A | | 2/2000 | Greenberg et al. |
| 6,090,296 A | | 7/2000 | Oster |
| 6,094,767 A | | 8/2000 | Iimura |
| 6,103,363 A | | 8/2000 | Boire et al. |
| 6,110,528 A | | 8/2000 | Kimura et al. |
| 6,117,337 A | | 9/2000 | Gonzalez-Martin et al. |

* cited by examiner

Primary Examiner—Krisanne Thornton
(74) Attorney, Agent, or Firm—Glasgow Law Firm, PLLC

(57) ABSTRACT

An ultraviolet (UV) disinfection system and method for treating for treating waste-containing fluids including a configuration and design to function effectively with at least one UV light source or lamp that is not submerged in the fluid. The UV light source is positioned outside the fluid to be disinfected via exposure to at least one UV dose zone outside the fluid being treated wherein UV light is projected into the at least one dose zone. The UV light source may be presented in a vertical riser configuration, wherein the UV light source is positioned above the fluid to be treated and projecting a UV dose zone downward toward and into the fluid to be treated, with the fluid moving upward toward the UV light source. At least one interface plate is used to provide a surface zone for UV disinfection above the fluid and to provide additional treatment means for balancing pH, affecting effluent chemistry, reducing organic chemicals, and the like. Alternatively, the UV light source may be presented in a planar or horizontal design, wherein the UV light source is positioned above the fluid to be treated and projecting a UV dose zone downward toward and into the fluid to be treated, with the fluid moving in a direction substantially perpendicular to the UV dose zone. Thirdly, the UV light source may be presented in a reservoir configuration, wherein the UV light source is positioned above the fluid to be treated that is contained in a reservoir.

69 Claims, 8 Drawing Sheets

ULTRAVIOLET WASTEWATER DISINFECTION SYSTEM AND METHOD

CROSS-REFERENCE TO RELATED APPLICATIONS

This non-provisional utility patent application claims the benefit of one or more prior filed co-pending non-provisional applications; a reference to each such prior application is identified as the relationship of the applications and application number (series code/serial number): The present application is a Continuation-In-Part of application Ser. No. 09/630245, filed Jul. 31, 2000, which is incorporated herein by reference in its entirety.

BACKGROUND OF THE INVENTION (1) Field of the Invention

The present invention relates generally to a system and method for ultraviolet disinfection and, more particularly, to a system and method for ultraviolet disinfection of waste-containing fluids.

(2) Description of the Prior Art

Mechanism of Action

It is well known in the art to use ultraviolet light (UV) for the disinfection treatment of water. Ultraviolet light, at the germicidal wavelength of 253.7 nanometers, alters the genetic (DNA) material in cells so that bacteria, viruses, molds, algae and other microorganisms can no longer reproduce. The microorganisms are considered dead, and the risk of disease from them is eliminated. As the water flows past the UV lamps in UV disinfection systems, the microorganisms are exposed to a lethal dose of UV energy. UV dose is measured as the product of UV light intensity times the exposure time within the UV lamp array. Microbiologists have determined the effective dose of UV energy to be approximately about 34,000 microwatt- seconds/cm2 needed to destroy pathogens as well as indicator organisms found in wastewater. Typical prior art disinfection systems and devices emit UV light at approximately 254 nm, which penetrates the outer cell membrane of microorganisms, passes through the cell body, reaches the DNA and alters the genetic material of the microorganism, destroying it without chemicals by rendering it unable to reproduce.

Ultraviolet light is classified into three wavelength ranges: UV-C, from about 200 nanometers (nm) to about 280 nm; UV-B, from about 280 nm to about 315 nm; and UV-A, from about 315 nm to about 400 nm. Generally, UV light, and in particular, UV-C light is "germicidal," i.e., it deactivates the DNA of bacteria, viruses and other pathogens and thus destroys their ability to multiply and cause disease, effectively resulting in sterilization of the microorganisms. Specifically, UV "C" light causes damage to the nucleic acid of microorganisms by forming covalent bonds between certain adjacent bases in the DNA. The formation of these bonds prevents the DNA from being "unzipped" for replication, and the organism is unable to produce molecules essential for life process, nor is it able to reproduce. In fact, when an organism is unable to produce these essential molecules or is unable to replicate, it dies. UV light with a wavelength of approximately between about 250 to about 260 nm provides the highest germicidal effectiveness. While susceptibility to UV light varies, exposure to UV energy for about 20 milliwatt-seconds/cm$^2$ is adequate to deactivate 99 percent of the pathogens.

Prior Art

Ultraviolet light has a proven track record of killing bacteria and viruses found in municipal wastewater. In addition, environmental concerns over the use of chemical disinfectants, coupled with improvements in ultraviolet-lighting teclnology, have led to the development of UV systems that treat spent metalworking fluids in the industrialized world; disinfect drinking water in developing countries; and clean aquaculture water, ballast water, and hospital air everywhere. Typically, chlorine gas or liquid is injected by a high-speed inductor directly into wastewater to kill bacteria before the water is discharged. According to industry experts, the main advantage of using UV instead of standard disinfection techniques is elimination of the transport and use of chlorine possible with the UV light-based system.

Unfortunately, evidence is mounting that organic chemical by products of chemical disinfection, especially byproduct of chlorination such as dioxane, are carcinogens and/or toxins for humans. Therefore, chemical disinfection is not a viable alternative when chemical purity of the fluid is desired and/or required. Additionally, in spite of this toxicological evidence, the EPA has recently been forced to relax restrictions on certain known carcinogenic chlorination by-product, such as chloroform. Additionally, other chemicals, such as the nitrate ion, have been shown to negatively influence the development of children.

In light of the emerging, data concerning the toxicity of organic and inorganic chemicals and the relaxation of water purity regulations, reducing the discharge into the environment of these compounds is of growing concern. However, removal of these compounds requires the use of extremely expensive methods, such as filtration through activated charcoal or similar. Thus, there exists a need for a system that can easily remove or eliminate organic and inorganic compounds from wastewater.

Used properly, ultraviolet light effectively destroys bacteria, viruses and other microorganisms in water and wastewater, without using chemicals. By doing away with need to worry about operator safety or the requirement for buildings for storage and handling of dangerous solutions and gases. Costly liability insurance premiums are significantly reduced. Testing of effluent for chlorine residual is no longer necessary, and toxicity problems associated with chlorine use are eliminated. Another factor leading municipalities to reconsider chlorination is its increased cost due to the national Uniform Fire Code adopted in 1993, which specifies expensive requirements for double containment of stored chlorine and chemical scrubbers in case of leaks.

Prior art applications of UV light used for disinfection of water include private drinking water supplies, municipal drinking water treatment plants, industrial product and process waters, and commercial applications, and wastewater treatment in primary, secondary, and tertiary treatment process for industrial, commercial and municipal wastewater treatment applications.

While UV purification is well suited for many residential, commercial, industrial and municipal water and wastewater treatment applications, considerations of the water quality and about the desired or required effluent purity impact the system design and performance. Prior art UV disinfectant systems work best when the water temperature is between about 35 and about 110 degrees Fahrenheit, since extreme cold or heat will interfere with the UV system performance.

The UV light source used in prior art arc typically low pressure mercury lamps, which can effectively clean water of dangerous and illness-causing viruses and bacteria, including intestinal protozoa such as Cryptosporidium, Giardia, and *E.coli*, provided that the proper number and configuration of lamps are included in the system. All known prior art systems calculate, design and configure the proper number and arrangement or positioning of lamps as set forth and described by formulas developed and published by Dr. George Tchobanoglous, presently of University of California at Davis.

Dr. George Tchobanoglous, professor emeritus of civil and environmental engineering at the University of California, Davis and former chairperson on a committee of academic, industrial, and environmental consultants who drafted guidelines on UV disinfection for California in 1994, is perhaps the leading authority on UV water disinfectant systems and methods used in the prior art. His formulas for predicting the minimum required number of UV lamps and configuration of same are based on a key component of positioning the UV lamps within the water to be treated, and more particularly, requiring a lamp centerline-to-centerline distance of not more than three (3) inches to ensure effective disinfectant UV dosage for any influent system and flow rate; these formulas referred to as "point source summation".

Traditional low-pressure UV systems found in the prior art are used for low flow water disinfection or smaller projects with air and surface applications. The low pressure UV lamp treats between 10 and 180 gallons per minute of fluid using up to 12 lamps at a time. As flows increase or higher UV doses are required, the multiple low-pressure lamp concept becomes complex and cumbersome. The medium pressure UV lamp offers a solution to maintain simplicity and cost effectiveness in meeting the higher flow and higher dose challenge. A single medium pressure UV lamp can treat up to 2,300 gallons per minute of fluid. Notably, the UV disinfection systems and methods used by prior art consistently involve and teach the use of low pressure UV lamp and equipment for water, air and surface disinfection applications. These prior art systems require treatment chambers, usually constructed of stainless steel. The prior art air systems also use low-pressure UV lamps and treat air in storage tanks.

Where the prior art uses a medium pressure UV lamp, typically single lamp units are used, possibly capable of treating 10 to 2,300 gallons per minute of fluid. In these cases, prior art requires special enhanced medium pressure UV lamps, with these applications restricted for use treating high and low temperature fluids that are unachievable with low-pressure lamps. Even with such configurations, the use of immersion-positioned UV lamps in an effective chamber design still requires system downtime to change the UV lamp. Special enhanced UV lamp design is required to achieve the highest performance in TOC reduction, ozone removal and chlorine destruction.

Problems exist for prior art systems where factors are present that inhibit UV light from penetrating the water. Turbidity, which is the state of water when it is cloudy from having sediment stirred up, interferes with the transmission of UV energy and decreases the disinfection efficiency of the UV light disinfection system. In cases where the water has high iron or manganese content, is clouded and/or has organic impurities, it is usually necessary to pre-treat the water before it enters the UV disinfection stage because deposits on the quartz-encased UV lamps, which are immersed in the water to be treated, interfere with the UV light transmission, thereby reducing the UV dose and rendering the system ineffective. Prior art typically employs UV purification in conjunction with carbon filtration, reverse osmosis and with certain chemicals to reduce fouling between cleanings of the quartz sleeves that surround the UV lamps.

Typically, prior art devices and systems for disinfecting water via ultraviolet light exposure commonly employ standard ultraviolet light sources or lamps encased in quartz sleeves and suspended in the water being treated. Benefits of using ultraviolet light for disinfecting water, particularly waste water treatment, include the following: no chemicals, like chlorine, are needed to ensure effective water disinfection provided that the proper number of lamps are used and properly positioned for a given influent and flow rate; since no chemicals are required in the disinfection process, no storage and/or handling of toxic chemicals is required; no heating or cooling is required to ensure disinfection; no storage tanks or ponds are necessary because the water can be treated as it flows through the system; no water is wasted in the process; no change in pH, chemical or resistivity of the water being treated; approximately at least 99.99% of all waterborne bacteria and viruses are killed via UV light exposure for disinfection; thereby providing increased safety of using the system and effectiveness of same.

As set forth in the foregoing, prior art UV water treatment systems disinfect and remove microorganisms and other substances from untreated, contaminated water sources and produce clean, safe drinking water. The core technology employed in WaterHealth International's system is includes a patented, non-submerged UV light. This technology is claimed by WHI to be a recent and tested innovation developed at the Lawrence Berkeley National Laboratory, a premier, internationally respected laboratory of the U.S. Department of Energy managed by the University of California. This prior art system delivers a UV dose of up to 120 $mJ/cm^2$, which is more than three times the NSF International requirement of 38 $mJ/cm^2$ and exceeds World Health Organization and EPA water quality standards and effectively treats bacteria, viruses and CR-yptosporidiunm in drinking water. In addition, recent research conducted at two different laboratories indicates that UV doses of 10 $mJ/cm^2$ or less produce 4-log reductions in Giardia. Based on this research, UV dosage of up to 120 $mJ/cm^2$ greatly exceeds the dosage required for inactivation of Giardia. Additional components included in WaterHealth International's systems effectively treat specific problems such as turbidity, silt, tastes, odors and various chemicals. Significantly, WHI's systems are not intended to treat raw sewage or wastewater.

Among applications for UV disinfection systems for water include wastewater treatment and surface treatment. By way of example and explanation, disinfection of municipal wastewater using UV light avoids problems associated with storage, transport and use of chemicals and associated regulation for them. UV disinfection is safe, cost effective and applicable to tertiary treated effluent as well as secondary, primary, and combined sewer overflows (CSO) and storm water. Ultraviolet light can help improve shelf life of products and allow processors to reduce chemical additives in wash water without sacrificing, high levels of disinfection. UV light provides non-chemical microbial control for captive water loops without altering the taste, color or odor of the food. Environmentally safe UV disinfection is one of the few water treatment methods unburdened by regulatory restrictions, consumer/environmental group concerns or high operation costs.

By way of comparison between prior art UV disinfection systems and traditional chlorine-based disinfection, the commercially available Trojan UV system can disinfect more consistently and effectively than is possible with current chlorination procedures, with significantly less cost per gallon. The UV treatment takes approximately 6–10 seconds in a flow-through channel, while chlorine requires 15–20 minutes treatment time in acontact tank. According to Trojan literature, LV disinfection can greatly reduce capital and operating costs. With UV treatment, it is possible to eliminate the need for large contact tanks designed to hold peak flows. Space requirements are reduced and no buildings are needed since the entire process and related commercially available equipment are designed to operate outdoors.

However, cleaning and maintenance of the quartz sleeves, which are necessary and essential to protect the UV lamp or light source used in nearly all prior art systems, can be come a time-consuming duty, especially when working with multi-lamp low pressure systems. During operation while the UV lamps and quartz sleeves are suspending in the water to be treated, minerals and contaminants in the water deposit onto the quartz sleeves, thereby causing fouling on the sleeve surface. This fouling reduces the effectiveness of the UV lamps because the fouling interferes with the UV light transmission into the water. To save time and prevent quartz sleeve fouling a cleaning mechanism can be supplied for either manual or automatic operation, like using wiper glides over the sleeves to remove deposits, which may block the light emitted from the UV lamp. This provides improved performance and reduces maintenance time, but only where the water quality is low. In every case, the UV lamps encased in quartz sleeves must be removed for cleaning on at least a monthly basis, depending on specifics of a given system and its influent and flow rates. The cleaning requires the system to be shut down temporarily or diverted to other UV lamps, so system shut down decreases capacity and/or increases operating costs. Furthermore, the quartz sleeve-encased lamps are extremely heavy, requiring the use of a crane to raise them out of the water flow stream for cleaning. Cranes and crane time are expensive, thereby increasing overall system costs. Only one company, WaterHealth, Inc., might in any way suggest the use of non-submerged lamps for UV systems but these are limited expressly in advertising literature as applicable only and exclusively in applications that do not require high purification, e.g., previously purified drinking water but not wastewater treatment.

These prior art systems do not employ optical components nor reflective materials or photocatalytic materials in the holding tank and reaction vessels.

Thus, there remains a need for a UV disinfection system for treating waste-containing fluids having reduced maintenance time and costs, increased flow rates for a given disinfection level, and overall lower equipment, installation, and system costs. Additionally, there remains a need for water purification system that can remove or degrade organic compounds and other chemical contaminants in fluids with reduced maintenance and expense.

SUMMARY OF THE INVENTION

The present invention is directed to a UV disinfection and chemical reduction system and method for treating waste-containing fluids, particularly wastewater, whereby the UV light or other activating wavelengths can effectuate catalytic reduction of water-borne chemicals and the UV light source requires less maintenance and cost than prior art systems and devices while providing at least the same disinfection level for a given influent and flow rate thereof.

One object of the present invention is to provide a UV disinfection system for treating waste-containing fluids configured and arranged to function effectively with at least one UV light source or lamp that is not submerged in the fluid to be disinfected. The UV light source is positioned outside the fluid to be disinfected via exposure to at least one UV dose zone wherein UV light is projected into the zone.

Another object of the present invention includes presentation of the UV light source presented in at least two primary configurations: a vertical riser configuration and a planar or horizontal configuration. In the vertical riser configuration the UV light source is positioned above the waste-containing fluid to be treated and projecting a UV dose zone downward toward and into the waste-containing fluid to be treated, with the waste-containing fluid moving upward toward the UV light source. Alternatively, the UV light source may be presented in a planar or horizontal design, wherein the UV light source is positioned above the waste-containing fluid to be treated and projecting a UV dose zone downward toward and into the waste-containing fluid to be treated, with the waste-containing fluid moving in a direction substantially perpendicular to the UV dose zone.

Still another object of the present invention is to provide a UV dose zone including at least one zone, more preferably four zones, wherein one zone includes an interface zone positioned between the UV light source and the fluid to be treated and another zone includes a reaction zone positioned within the fluid. The reaction zone may be formed by an interface plate that incorporates catalytic properties to enhance desired reactions.

The present invention is further directed to a method for treating waste-containing fluids by disinfecting those waste-containing fluids using UV light projected by at least one UV light source producing at least one dose zone, the UV light source being positioned outside the waste-containing fluid.

Accordingly, one aspect of the present invention is to provide a system and method for disinfecting waste-containing fluid including at least one UV light source positioned outside the waste-containing fluid to be treated with the at least one UV light source producing at least one UV dose zone for disinfecting the waste-containing fluid.

Another aspect of the present invention is to provide a system and method for disinfecting and purifying fluid including at least one UV light source positioned outside the fluid to be treated with the at least one UV light source producing four UV dose zones for disinfecting the fluid, with one zone provided at an interface zone, and one zone provided at a reaction zone positioned between the UV light source and the fluid to be treated. The reaction zone may be formed by an interface plate that incorporates catalytic properties to enhance desired reactions Still another aspect of the present invention is to provide a system and method for disinfecting waste-containing fluid including at least one UV light source positioned outside the waste-containing fluid to be treated with the at least one UV light source producing at least one U-V dose zone for disinfecting the waste-containing fluid, wherein the at least one UV light source is a medium-to-high intensity UV light source or spectral calibration lamp.

These and other aspects of the present invention will become apparent to those skilled in the art after a reading of the following description of the preferred embodiment when considered with the drawings.

DETAILED DESCRIPTION OF THE PREFERRED EMBODIMENTS

Figure 1:
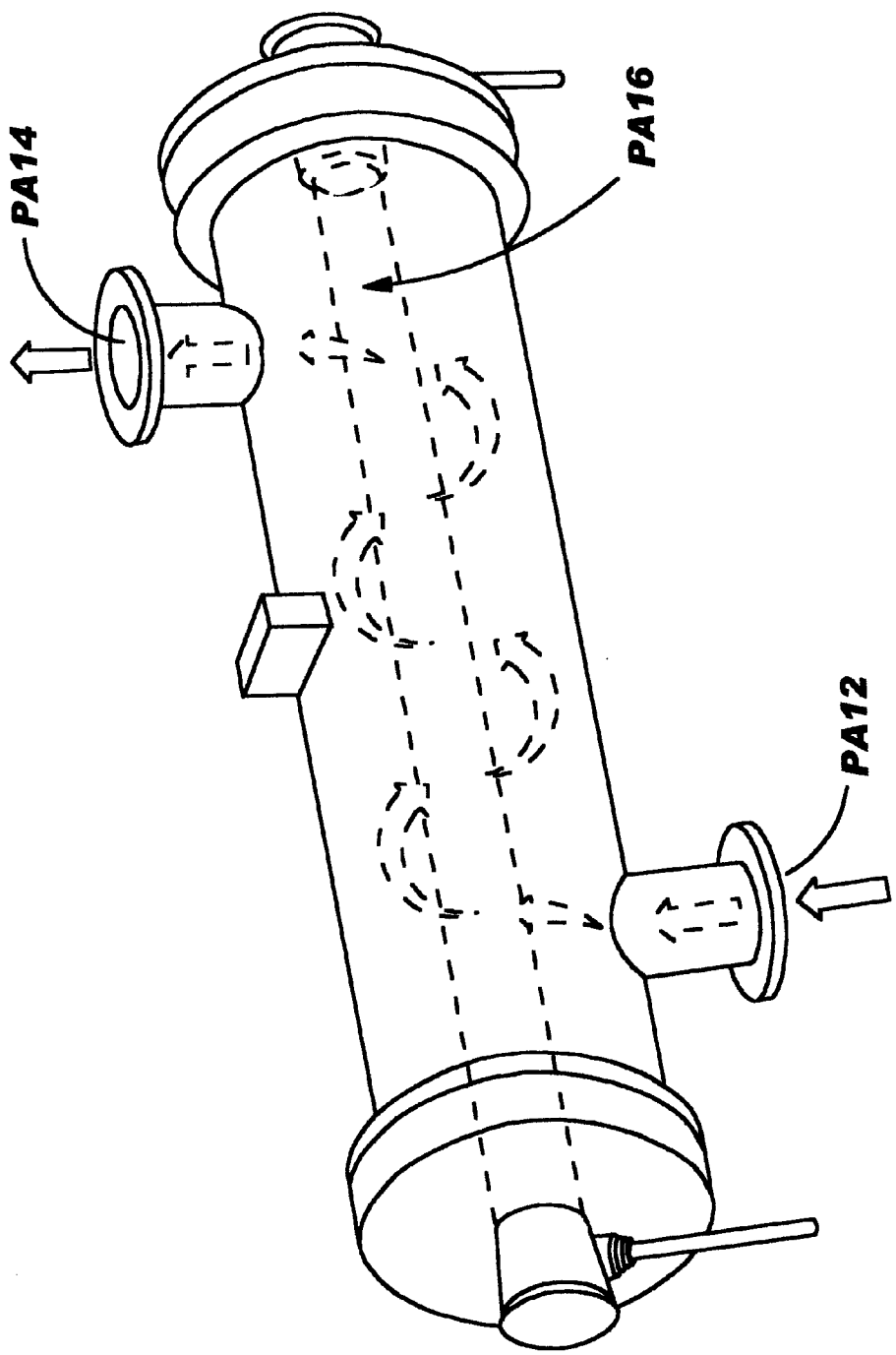
FIG. 1 is an illustration of PRIOR ART in a side view.

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting, terms.

Referring now to the drawings in general, the illustrations are for the purpose of describing a preferred embodiment of the invention and are not intended to limit the invention thereto. FIG. 1 shows a prior art system for ultraviolet (UV) disinfection of a waste-containing fluid wherein the UV light source PA16 is submerged in the waste-containing fluid. Untreated influent PA12 enters the system flowing past the submerged light source and exits the output as treated disinfected effluent PA14. By contrast to prior art, the present invention is directed to an ultraviolet (UV) disinfection system and method for treating fluids including a configuration and design to function effectively with at least one UV light source or lamp that is not submerged in the fluid.

Advantageously, the non-submerged configuration of the present invention prevents the problems associated with breakage of the lamp and/or lamp housing and fouling of the lamp housing. Additionally, the non-submerged configuration of the present invention prevents the problems associated with extreme temperatures in the fluid. Fluorescent lamps, including UV lamps, lose a significant amount of output at low temperatures. Thus, a non-submerged system, which separates the lamp from the fluid to be treated, allows for the temperature of the lamp to be maintained at more optimal temperature, without necessitating cooling or heating the fluid as well. Thus, this system more efficiently disinfects extreme environments, such as freezers, coolers, hot water heaters, and the like.

Vertical Riser Configuration (VRC)

Figure 2:
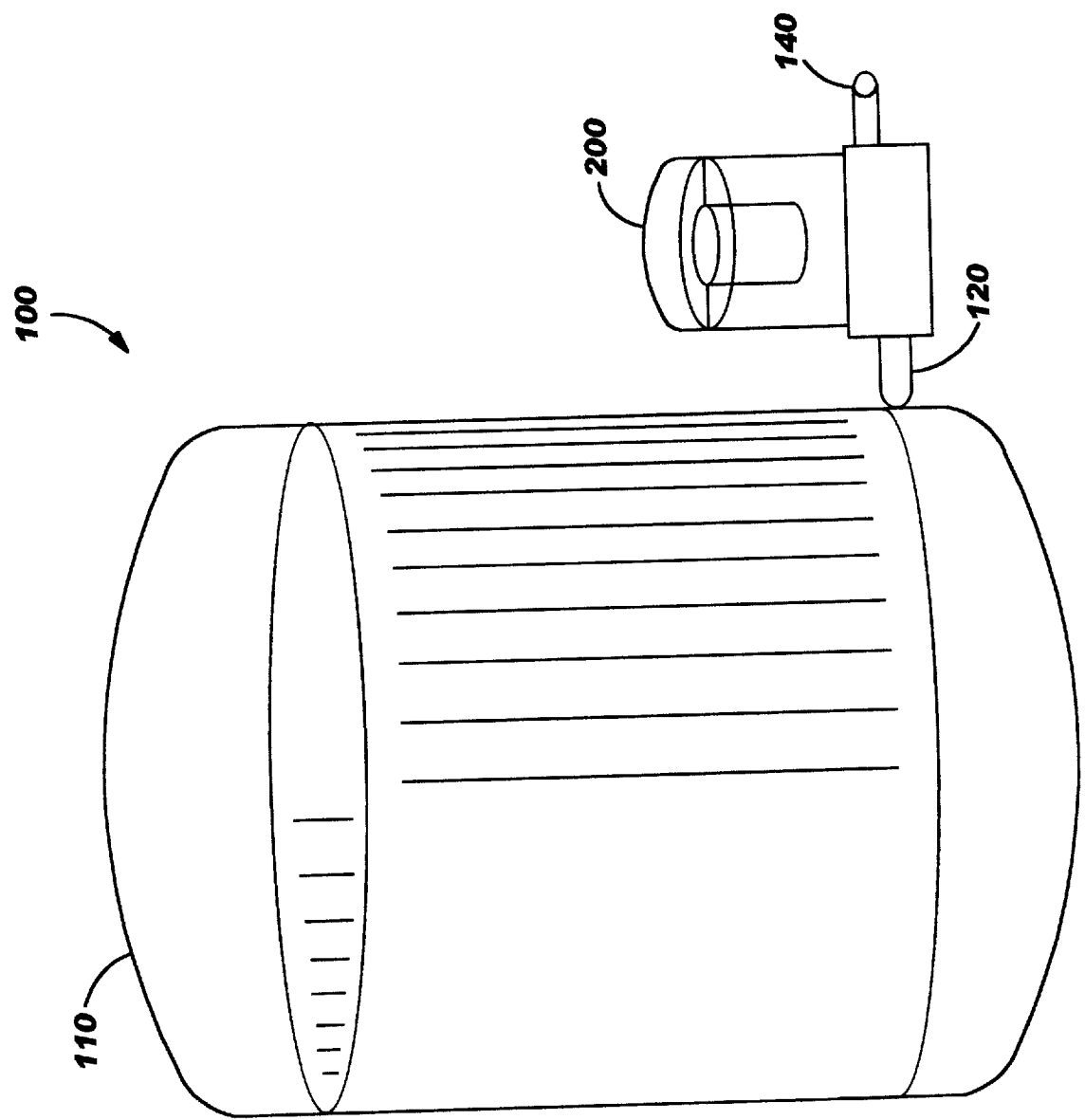
FIG. 2 is an illustration of a side view of a UV disinfection system constructed according to the present invention in a vertical riser configuration.
Figure 3:
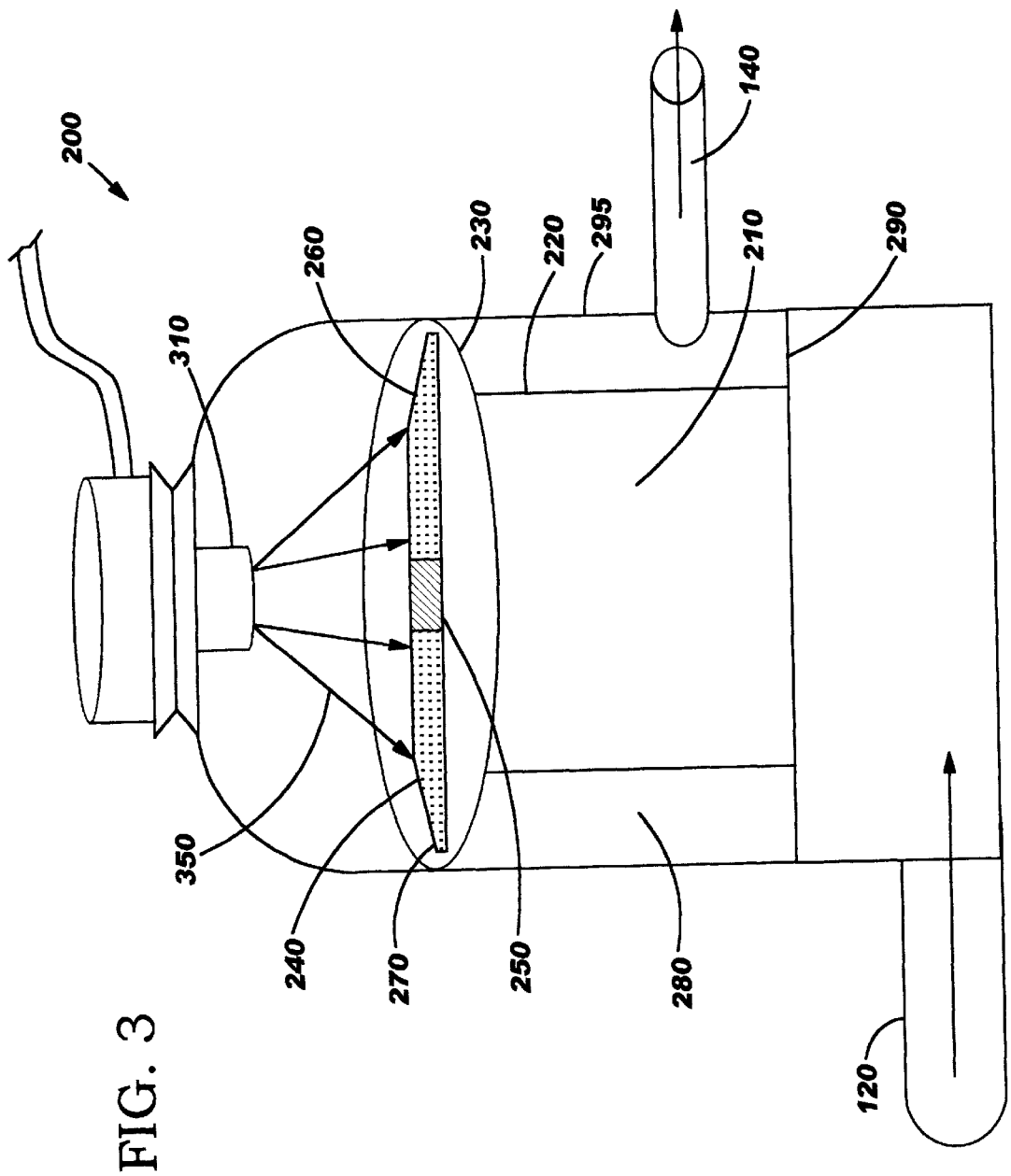
FIG. 3 is an illustration of an exploded side view of the embodiment shown in FIG. 2.

The UV light source may be presented in a vertical riser configuration according to a preferred embodiment of the present invention, as shown generally at 100 in FIG. 2, wherein the fluid exits a reservoir or holding container 110 via a pipe or outlet 120 into the vertical riser configuration (VRC) 200 and passes therethrough prior to discharge from the pipe or outlet 140 for consumption or end use. Furthemore, the VRC, as shown generally at 200 in FIG. 3, includes at least one UV light source 310. This UV light source 310 is part of a lamp assembly, as shown generally at 300 in FIG. 5. The lamp assembly 300 is composed of a housing 320 that encases the UV light source 310, UV light rays 330, at least one optical component 340, and UV light ray output 350 that exits the housing. Referring to FIG. 3, the UV light ray output 350 exits the housing above the fluid 210 to be treated, this fluid entering the VRC from the outlet pipe 120 of the holding container or reservoir 110 and being forced upward through the interior pipe 220 of the VRC 200 toward the UV light ray output 350 that is projected downward toward the fluid surface 230 and into the fluid 210 to be treated, once again with the fluid moving upward toward the UV light source 310. At least one interface plate 240 may be fitted to the top of the interior pipe 220, thus increasing the exposure time of the fluid 210 to the UV light ray output 350. The at least one interface plate 240 contains a hole or holes 250 that allows fluid rising upward through the interior pipe 220 to exit at the top of the pipe. The fluid then traverses across the superior surface 260 of the interface plate 240 to the plate edge 270, where it then descends into the exterior chamber 280 of the VRC. The fluid is prevented from returning into the interior pipe 220 by a base plate 290 that solidly connects the exterior of the interior pipe 220 with the interior of the outer pipe 295. The fluid then exits the VRC 200 through the pipe or outlet 140. The UV light rays 330 may be projected downward from a UV light source or a lamp system 310 that includes optical components. These optical components may include, but are not limited to, reflectors, shutters, lenses, splitters, focalizers, mirrors, rigid and flexible light guides, homogenizer or mixing rods, manifolds and other couplers, filters, gratings, diffracters, color wheels, and the like. These optical components are internal to the lamp system and are positioned between the UV light source or lamp 310 and the UV ray light output 350 of the lamp assembly 300, thereby focusing, directing, and controlling the light ray output 350 that irradiates the fluid 210 and that sterilizes any microorganisms that exist in the fluid 210. The UV light ray output 350 irradiates and may also be transmitted through the fluid 210. UV light ray output 350 that is transmitted through the fluid and strikes the reflective interior surfaces (not shown) of the VRC components is reflected back into the fluid where it may strike microorganism. The reflection of the UV light ray output 350 back into the fluid by the reflective interior surfaces of the VRC components enhances the killing capacity of the VRC system 200.

Additionally, the interface plate may possess catalytic properties such that certain reactions are catalyzed in the vicinity of the interface plate. For example, $TiO_2$ may be incorporated into the interface plate that is made of glass or other appropriate material. When such a plate is irradiated with UV light, fatty acids and other organic chemicals are chemically reduced, resulting in degradation to smaller volatile products such as methane, ethane, etc. Additionally, nitrate ion is reduced to elemental nitrogen in such a system. Thus, the incorporation of $TiO_2$ into the interface plate with subsequent UV irradiation reduces the levels of two potential human toxins—organic chemicals and nitrate ion. The interface plate may also perform mechanical or other physical functions. For example, the plate may grind and/or sift particles contained within the fluid. The plate may also provide cooling, heat, steam, or gas(es) to the reaction zone to enhance desired reactions or inhibit undesired reactions. Heat, steam, or other gases may also be added in order to increase the vapor zone. In general, the interface plate can be used to facilitate surface reactions and/or surface/air reactions.

Advantageously, the disinfected, purified water that exits the total system from the VRC device is completely free from microorganisms without requiring the addition of chemicals or other additives that would increase the total dissolved solids in the water.

Reservoir Configuration

Figure 4:
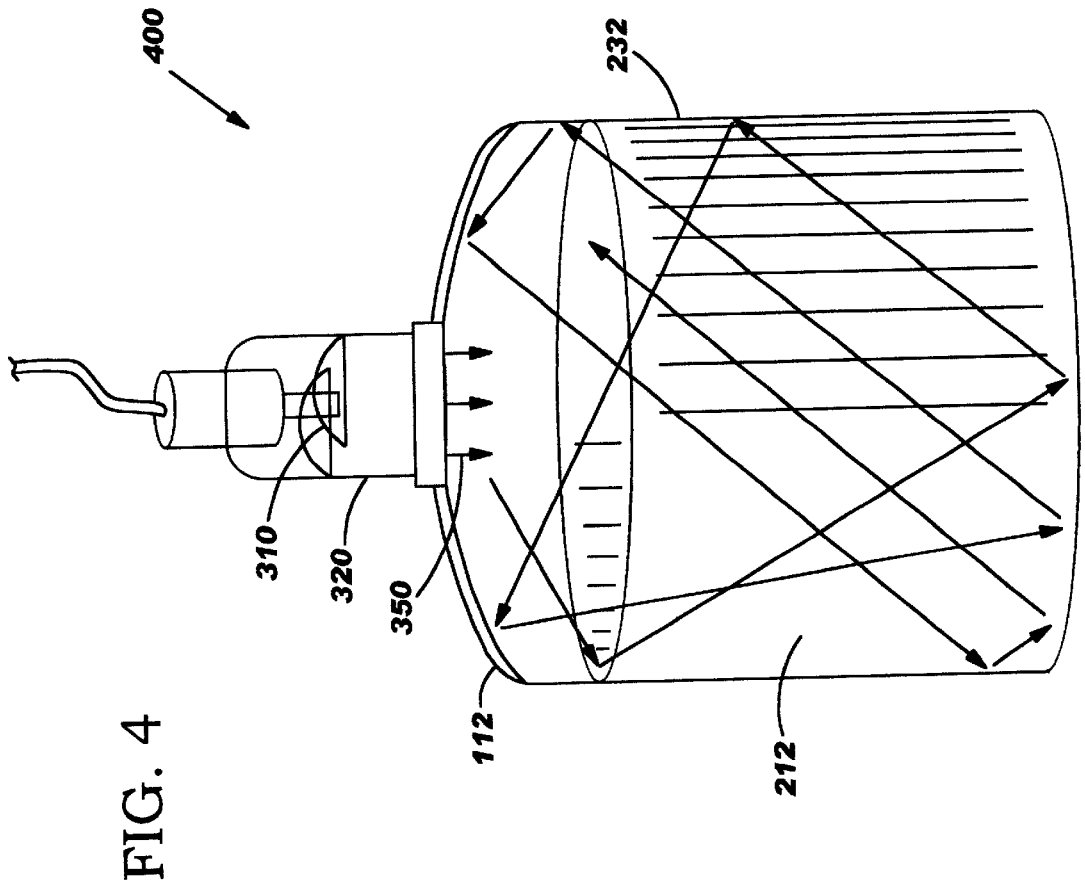
FIG. 4 shows an illustration of a UV disinfection system of an alternative embodiment of the present invention.
Figure 5:
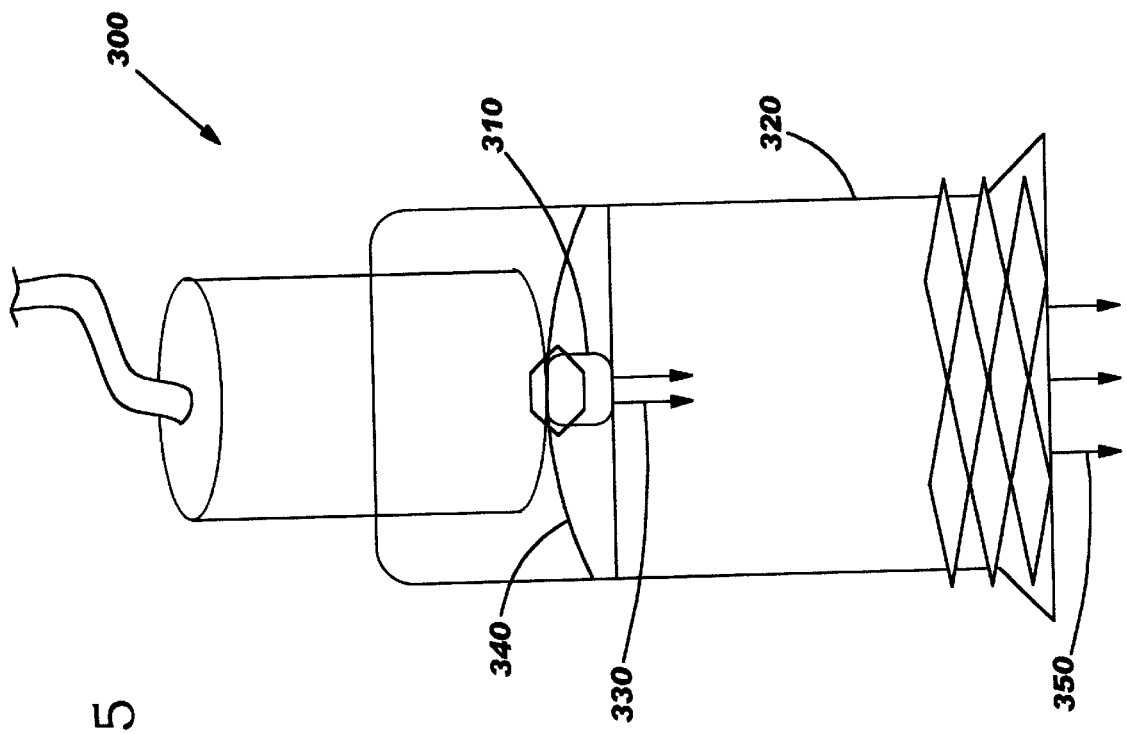
FIG. 5 is an illustration of an exploded side view of the embodiment shown in FIG. 4.

Alternatively or in combination with the VRC system, a non-VRC configuration is advantageously constructed and configured to provide UV disinfection from a non-submerged UV light source for a reservoir, holding container, or other non-flowing water storage, however temporary the water dwell time may be. Preferably, the fluid is pre-treated water that has already been disinfected and purified, possibly with low total dissolved solids therein. This pretreatment may have occurred in a VRC system that incorporates a catalytic plate to reduce organic and inorganic contaminants in the water, in addition to disinfecting the water. As illustrated in FIGS. 4 & 5, the present invention, generally referenced 400, is a non-riser configuration (NRC) that includes at least one UV light source 310. This UV light source 310 is part of a lamp assembly, as shown generally at 300 in FIG. 5. The lamp assembly 300 is composed of a housing 320 that encases the UV light source 310, UV light rays 330, at least one optical component 340, and UV light ray output 350 that exits the housing. Referring to FIG. 4, the UV light ray output 350 exits the housing 320 above the fluid 212 to be treated, this fluid being held in a holding container or reservoir 112 and not being forced toward UV light ray output 350 that is projected downward toward the fluid surface 232 and into the fluid to be treated 212, once again with the fluid 212 not being forced toward the UV light source 310. The UV light ray output 350 may be projected downward from a UV light source or a lamp system 300 that includes optical components as previously described. These optical components may include, but are not limited to, reflectors, shutters, lenses, splitters, focalizers, mirrors, rigid and flexible light guides, homogenizer or mixing rods, manifolds and other couplers, filters, gratings, diffracters, color wheels, and the like. These optical components are internal to the lamp system and are positioned between the UV light source or lamp 310 and the UV ray light output 350 of the lamp system 300, thereby focusing, directing, and controlling the light ray output 350 that irradiates the fluid 212 and that sterilizes any microorganisms that exist in the fluid 212. The UV light ray output 350 irradiates and may also be transmitted through the fluid 212. UV light ray output 350 that is transmitted through the fluid and strikes the reflective interior surface of the holding tank or container 112 is reflected back into the fluid where it may strike microorganism. The reflection of the UV light ray output 350 back into the fluid by the reflective interior surface of the holding tank or container 112 enhances the killing capacity of the NRC system 400.

Planar Configuration

Alternatively to the vertical and reservoir configurations, the UV light source may be presented in a planar or horizontal design (not shown), wherein the UV light source is positioned within a UV light source system, including optical components, above the waste-containing fluid to be treated and projecting a UV dose zone downward toward and into the waste-containing fluid to be treated, with the waste-containing fluid moving from the influent point in a direction substantially perpendicular to the UV light source toward the effluent point.

A key factor in the design of a UV disinfection system and method according to the present invention involves the integration of two main components, including the non-submerged UV light source system and the hydraulic system. The light source system includes a housing surrounding and supporting a UV light source or lamp having at least one optical component positioned and arranged to direct the UV light rays toward and through an output, thereby introducing UV light rays toward a waste-containing fluid for disinfection of the fluid.

The hydraulic system includes a hydraulic tube and pumping system for forcing the waste-containing fluid upward through the tube toward the light source(s). The present invention includes the use of hydraulic systems that comprise a transporter or pumping system, and at least one interface plate. The hydraulic system serves at least three functions: it carries wastewater influent to an interface and provides flow to at least one interface plate and discharges the treated influent water as effluent to rivers or streams. The VRC system may include quick-connect lamps and housings with a monitoring and indicator system that would indicate that a lamp had failed. Each riser may have an individual, dedicated lamp and optical system with overlap between neighboring lamps to eliminate dead zone. Each riser in the VRC system may also have a valve that shuts off the riser in case of failure.

Figure 6:
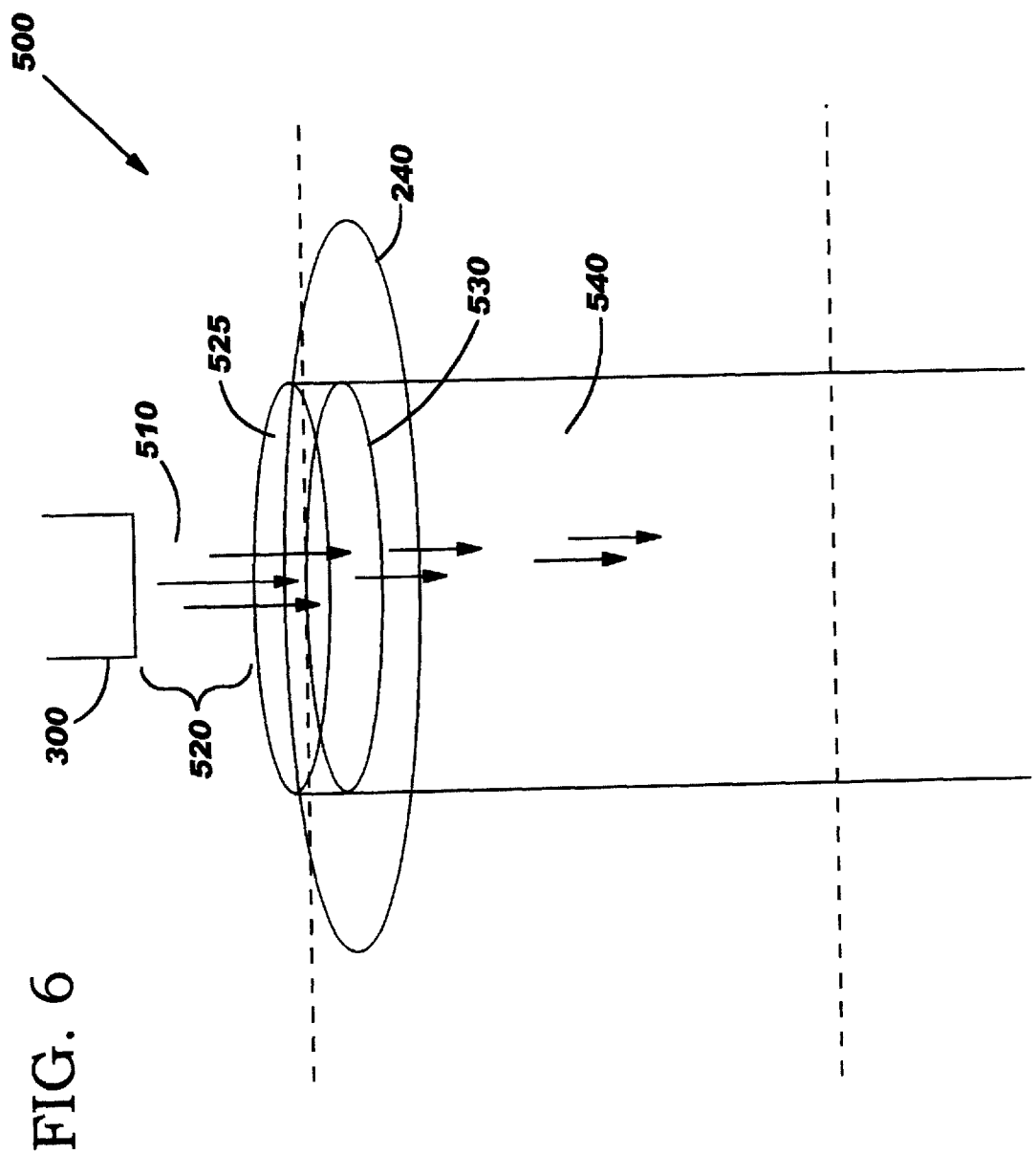
FIG. 6 is an illustration of the UV dose zones generated in a vertical riser configuration.

Advantageously, these systems have several UV dose zones established within them. In the VRC system, as best shown in FIGS. 3 and 5, the UV light source 310 is positioned within a UV light source system 300, including optical components as previously described, above the fluid to be treated and projecting a UV dose zone downward toward and into the fluid to be treated, with the fluid moving from the influent point 120, flowing vertically up the interior pipe 220 toward the UV light source 30, and then exiting the interior pipe 220 through the interface plate 240. The at least one UV light source is positioned above the fluid to be treated and projecting UV light ray output 350 downward toward and into the fluid to be treated, with the fluid moving upward toward the UV light source. Several UV dose zones are established within the VRC system, generally shown as 500 in FIG. 6. The first zone is the light source system exit UV dose zone 510, which occurs at the light source system and air interface. Then next zone is the air UV dose zone 520, which occurs just beneath the UV light source and just above the water and the at least one interface plate 240. The next zone is the vapor zone 525, which occurs just above the water surface. The next zone is the interface plate UV dose zone 530, which occurs at the intersection of the water and the at least one interface plate 240. The at least one interface plate is used to provide a reaction zone for UV disinfection of fluid flowing over the plate and to provide additional treatment means for balancing pH, affecting effluent chemistry, providing a catalyst, and the like. For example, $TiO_2$ may be incorporated into the interface plate to effect reduction of ions and compounds. Specifically, $TiO_2$ is used to reduce nitrates and nitrites to elemental nitrogen. Such a treatment is desirable, in that nitrates have been linked to developmental defects in children. Additionally, $TiO_2$ incorporated in glass and irradiated with UV light will degrade fatty acids and other organic compounds adjacent to exterior of the glass. Thus, such a plate can be used to degrade organic contaminants found in water. Additionally, UV light can catalyze a variety of reactions, and the use of UV light with any one or combination of the plethora of available chemical catalyst generates numerous possible catalytic combinations that are used to catalyze a myriad of desirable reactions. The photocatalyst may include photo-activated semiconductors such as Titanium Oxide; TiO2 (photo activation wavelength; not more than 388 nm), Tungsten Oxide; WO2 (photo activation wavelength; not more than 388 mm), Zinc Oxide; ZnO (photo activation wavelength; not more than 388 nm), Zinc Sulfide; ZnS (photo activation wavelength; not more than 344 nm) and Tin Oxide; SnO2 (photo activation wavelength; not more than 326 nm). In addition to these catalysts, other catalysts, such as $PtTiO_2$, are known. TiO2 may be preferably applied as the photocatalyst, considering that the activation power is very high, the catalyst is long-lived with high durability, and safety for human applications is certified, as TiO2 has been used safely for a long time in cosmetic and food applications. Additionally, the interface plate may be a biofilter, and contain enzymes or bacteria that react with substrates contained in the fluid.

The last zone is the submerged UV dose zone 540, which creates a variable UV dose zone that decreases in effectiveness at greater distances from the UV light source.

Figure 7:
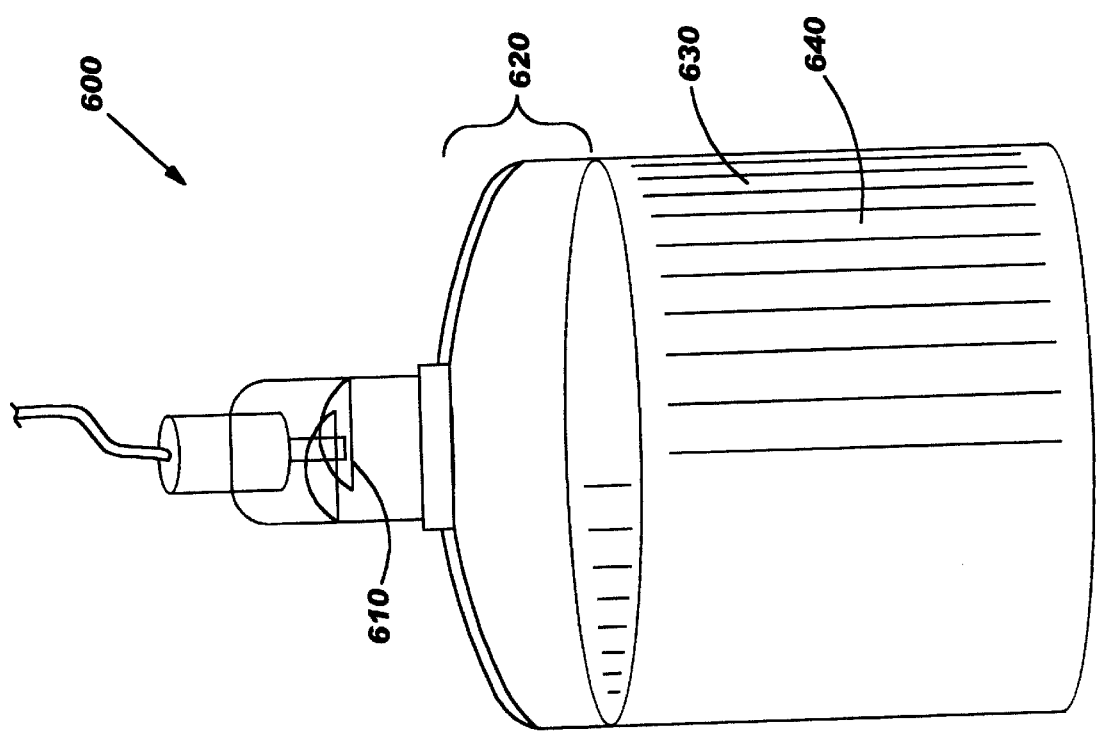
FIG. 7 is an illustration of the UV dose zones generated in an alternative embodiment of the present invention.

For the generally static non-riser configuration, the zones are different than those described in the VRC system. In the generally static non-riser system, generally shown as 600 in FIG. 7, the first zone is the light source system exit UV dose zone 610, which occurs at the light source system and air interface. Then next zone is the air UV dose zone 620, which occurs just beneath the UV light source and just above the water surface 230. The next zone is the vapor zone, which occurs just above the surface of the water. The last zone is the submerged UV dose zone 640, which creates a variable UV dose zone that decreases in effectiveness at greater distances from the UV light source.

For the planar configuration, the zones are different than the VRC and reservoir configurations. Several UV dose zones are established within the system (not shown). The first zone is the air UV dose zone that occurs just beneath the UV light source and just above the water. The next zone is the air/water interface UV dose zone that occurs at the air and water interface. The last zone is the submerged UV dose zone, which occurs within the flowing water.

While generally regarding the UV light source and configuration thereof, the preferred embodiment of the present invention includes at least one optical component positioned between the UV light source and the UV light source system output point. Advantageously, the use of optical components enables the system to maximize the intensity, focus, and control of the UV light rays at the output for any given UV light source or lamp. Also, optical components, including but not limited to reflectors, shutters, lenses, splitters, mirrors, rigid and flexible light guides, homogenizer or mixing rods, manifolds and other couplers, filters, color wheels, and the like, can be utilized in combination to achieve the desired control and output, as set forth in U.S. Pat. Nos. 6,027,237; 5,917,986; 5,911,020; 5,892,867; 5,862,277; 5,857,041; 5,832,151; 5,790,725; 5,790,723; 5,751,870; 5,708,737; 5,706,376; 5,682,448; 5,661,828; 5,559,911; D417,920 and co-pending applications Ser. Nos. 09/523,609 and 09/587,678 which are commonly owned by the assignee of the present invention, and which are incorporated herein by reference in their entirety. Additionally, optical component such as gratings, dichroic filters, focalizers, gradient lenses, and off-axis reflectors may be used.

With regard to light guides, these may be fiberoptic lines composed of acrylic, glass, liquid core, hollow core, core-sheath, or a combination.

With regard to lenses, several embodiments are envisioned. Imaging lenses, such as a parabolic lens, and non-imaging lenses, such as gradient lenses, may be used. A gradient lens collects light through a collecting opening and focuses it to an area smaller than the area of the collecting opening. This concentration is accomplished by changing the index of refraction of the lens along the axis of light transmission in a continuous or semi-continuous fashion, such that the light is "funneled" to the focus area by refraction. An example of gradient lens technology is the Gradium® Lens manufactured by Solaria Corporation. Alternatively, a toroidal reflector, as described in U.S. Pat. No. 5,836,667, is used. In this embodiment, a UV radiation source, such as an arc lamp, is located at a point displaced from the optical axis of a concave toroidal reflecting surface. The concave primary reflector focuses the radiation from the source at an off-axis image point that is displaced from the optical axis. The use of a toroidal reflecting surface enhances the collection efficiency into a small target, such as an optical fiber, relative to a spherical reflecting surface by substantially reducing aberrations caused by the off-axis geometry. A second concave reflector is placed opposite to the first reflector to enhance further the total flux collected by a small target.

Additionally, more than one reflector may be used with a lamp. For example, dual reflectors or three or more reflectors, as taught in U.S. Pat. Nos. 5,706,376 and 5,862,277, may be incorporated into the preferred embodiment. These reflectors may also be splitting reflectors and/or cascading reflectors.

In general, the transmissive optical components are UV transmissive and the reflective optical components are UV reflective. Additionally, any of the optical components, including the housing, may be made of acrylic or similar materials that degrade over time when exposed to UV light. These components can be replaced when their performance has deteriorated to an unacceptable level.

Notably, any number of lamps including low pressure, medium pressure, high pressure, and ultra high-pressure lamps, which are made of various materials, e.g., most commonly mercury (Hg), can be used with the system configuration according to the present invention, depending upon the fluid or influent characteristics and flow rates through the system. Furthermore, while high and ultra high pressure lamps have not been used commercially to date by any prior art system, predominantly because of the low energy efficiency associated with them and the lack of capacity for prior art design and configuration formulas to include high pressure UV lamps, the present invention is advantageously suited to accommodate medium to high to ultra high pressure lamps. In particular, a preferred embodiment according to the present invention employs medium to high-pressure UV lamps, more preferably high-pressure UV lamps. The present invention is advantageously suited to accommodate medium to high to ultra high pressure lamps, all of which can be metal, halogen, or a combination metal halide. Additionally, spectral calibration lamps, electrodeless lamps, and the like can be used.

In particular, a preferred embodiment according to the present invention employs a pencil-type spectral calibration lamp. These lamps are compact and offer narrow, intense emissions. Their average intensity is constant and reproducible. They have a longer life relative to other high wattage lamps. Hg (Ar) lamps of this type are generally insensitive to temperature and require only a two-minute warm-up for the mercury vapor to dominate the discharge, then 30 minutes for complete stabilization.

A Hg (Ar) UV lamp, which is presently commercially available and supplied by ORIEL Instruments, is used in the preferred embodiment according to the present invention. The ORIEL Hg(Ar) lamp, model 6035, emits UV radiation at 254 nm. When operated at 15 mA using a DC power supply, this lamp emits 74 microwatt/cm2 of 254 nm radiation at 25 cm from the source.

The system according to the present invention uses medium to high pressure UV lamps configured and functioning above the fluid or water flow, not immersed in the fluid flow as with all prior art systems designed for use in all water treatment applications. With this system, the number of lamps necessary to treat a given influent and flow rate can be reduced by perhaps a factor of ten, which is a major advantage in practical application. Also, the lamps are not susceptible to fouling, since they are not immersed in the fluid to be disinfected. Additionally, the design of the present invention allows for a significant reduction in heat in the water. Furthermore, the maintenance and servicing is greatly simplified. Also, in the vertical riser configuration according to one preferred embodiment configuration, the reactor design, which would comprise a number of cylindrical tubes oriented vertically, includes a hydraulic system having pumping equipment and a significant amount of pumping power. Furthermore, the present invention is an optical UV light source system for use in a waste-containing fluid disinfection system. As such, traditional mathematical models used for determining energy efficiencies for the present invention are inadequate and inapplicable. Thus, given the use of optical components associated with the UV light source, the use of medium to ultra high pressure UV lamps, and the introduction of at least one UV dose zone existing outside the water to be treated, the present system presents a revolutionary approach for designing, constructing, and operating a UV waste-containing fluid disinfection system that is nowhere taught or suggested in the prior art or mathematical models for predicting waste-containing fluid disinfection and flow rates thereof.

In one embodiment according to the present invention, the UV light source is a Fusion RF UV lamp, which is presently commercially available and supplied by Fusion UV Systems, Inc. The fusion lamp is a preferred lamp for a planar vertical riser system configuration, according to the present invention, to provide fast flow rates of the fluid treated within the system. This fusion lamp has a spectrum like a low-pressure lamp, having very strong UVB&C availability and output, but is a high power lamp having approximately 200 W/cm. Significantly, as set forth in the foregoing, no prior art teaches or suggests the use of high pressure lamps, in fact, all standard formulas, including those developed by Dr. George Tchobanoglous, for system design and operation use low pressure lamps.

Surprisingly, the attached data supporting the novelty and non-obviousness of the present invention shows that the UVB&C efficacy for a high-pressure lamp is about 7–8%, compared to about 20–21% for a Germicidal lamp, and about 5% for a medium pressure lamp. Thus, one Fusion lamp would replace about 40 germicidal lamps or about 20 medium pressure lamps by the following analysis:

[# lamps of type x]/[# lamps of type y]=[P/L(type y)]*[Efficacy (type y)]/[P/L(type x)]/[Efficacy (type x)][# MPL]/[# HPL]~ [200*8%]/[20*5%]~20[# LPL]/[# HPL]~[200*7%]/[2*21%]~40

Therefore, instead of having a facility with at least about 11,500 ea. 300 W MPLS as with prior art UV water disinfection systems, the present invention uses only a few hundred UV high-pressure lamps (HPL), depending on details of the design for a specific influent composition and flow rates desired for a given system. These results are surprising and not supported by prior art systems or the formulas used to design and configure them for effective operation. A variety of tubular lamp types may be used according to the present invention: Low Pressure (Power) germicidal Lamps (LPL), Medium Pressure (Power) Lamps (MPL), and Ultra-High Power Lamps (UHPL), to be used with water of various purity levels requiring differing dosing (Joules/liter) for disinfection, the surprising results supporting the use of medium to high pressure UV lamps for the UV disinfection system for water, according to the present invention, are established.

An additional advantage of high-power lamp systems is that extra-UV wavelengths, when delivered at sufficient intensity, may destroy or otherwise inactivate microorganisms as well. Several mechanisms of action are possible, but in general, the high-dose light denatures cell components such as proteins, cell membranes, and the like and inactivates the microorganism.

Additional considerations for a UV disinfectant system and method for treating water are installation cost, and lamp life. The lamp life for the Fusion lamp is approximately about 5000 hours, which is comparable to the low pressure lamps (LPL) and comparable to the life of the medium pressure lamp (MPL). The installation cost of the Fusion lamp is somewhat higher, but the maintenance and associated costs for operation is lower, thereby providing an overall lower cost system when compared with the prior art systems.

The system according to the present invention uses medium to high pressure UV lamps configured and functioning above the fluid or water flow. With this system, the number of lamps necessary to treat a given influent and flow rate can be reduced by perhaps a factor of ten, which is a major advantage in practical application. Also, the lamps are not susceptible to fouling, since they are not immersed in the waste-containing fluid to be disinfected. Additionally, the design of the present invention allows for a significant reduction in heat in the water. Furthermore, the maintenance and servicing is greatly simplified. Also, in the vertical riser configuration according to one preferred embodiment configuration, the reactor design, which would comprise a number of cylindrical tubes oriented vertically, includes a hydraulic system having pumping equipment and a significant amount of pumping power.

The present invention advantageously includes all of the above features, in particular because the UV lamps are separated from the flow stream and include a fiber optic delivery system, as well as using multi-kiloWatt lamps, like the Vortek Ultra-High Power Discharge (UHPD) lamps or similar commercial equivalent. The power range for these lamps is in the 10's of kilowatts to MegaWatt range. There geometry is cylindrical, like the medium power lamps, but they are roughly 1000 times more powerful. Advantageously, this lamp provides a much simpler facility, wherein servicing and maintenance are much easier and less frequently performed.

The flexibility of the UV waste-containing fluid disinfection system according to the present invention makes it possible to use lamp configurations similar to prior art systems for the overall geometry. However, the use of a much higher power lamp is preferred, thereby reducing the water treatment facility complexity and costs. This novel combination of higher pressure and power UV light sources in the present invention creates surprising results, even where prior art system configurations, i.e., horizontal flow-type configurations, are employed. Furthermore, the use of optical components within the UV light source system to focus, control, and increase the output intensity of the UV light rays introduced to the fluid to be disinfected increases the overall effectiveness of the present invention, even where the retrofit geometry is employed.

Thus, the present invention can be configured effectively either similarly to prior art-like system or retrofit geometry, i.e., a configuration of lamps above a horizontal flow stream while still surprisingly employing novel and non-obvious elements like UHPL and HPL in combination therewith, or in a clear departure and in complete differentiation from all prior art systems for all water treatment, having a configuration comprising the vertical riser geometry as shown in FIG. 2, including having at least one interface plate. In the retrofit geometry or configuration, there is a turbulence-inducing foil immersed in the flow stream below each lamp to assure that sufficient mixing occurs, thereby ensuring exposure of all of the microorganisms within the waste-containing fluid to the UV dose zone such that those microorganisms are sterilized. However, the use of the vertical riser configuration creates even more surprising results in that a multiplicity of UV dose zones are created as the fluid to be treated is forced via a hydraulic system toward the UV light source system, including UV light source or lamp and optical component(s).

Two main types of lamps are embodied according to the present invention for use therein as at least one light source for a given configuration. In particular, a tubular lamp is generally approximately about 1000 mm long, and between about 30 to about 60 mm diameter. A fusion lamp produces UV light output at about 250 mm and is approximately about 8 mm diameter in the middle and approximately about 14 mm diameter near the ends of the lamp. Alternatively, a high power, short arc (HP-SA) lamp figure is preferred in other configurations. Significantly, alternative lamp embodiments, including but not limited to alternative lamp design, power, and UV output efficiencies, and reasonable equivalents thereof may be substituted for these lamps identified herein as preferred embodiments without departing from the scope and teachings of the present invention.

Characteristics of and advantages to the present invention include at least the following: the use of Ultra High Power Lamps reduces complexity of illumination system, the lamps are isolated from the flow stream eliminating the fouling problem, since the UHPL, e.g., Vortek lamps, are immersed in their own flowing water cooling jackets (purified water), much of the heat will be dissipated in the Vortek-type lamp cooling system, probably eliminating the need for the heat-rejecting cold mirrors, since a much smaller number of parts are used (most likely less than 1% of the parts), the servicing costs are likely to be much lower. If the lamp life is longer for a given system constructed according to the present invention, the servicing costs are reduced by a similar factor as well.

The present invention allows a significantly simplified system, potentially significantly lower operating costs, and the capacity to process large quantities of water as well as relatively small quantities, as for home use. For a single-dwelling system, a single vertical riser UV light source system, is constructed and configured to be attached to the treated wastewater discharge. In this system, the UV light source is positioned within a UV light source system, including optical components, above the fluid to be treated and projecting a UV dose zone downward toward and into the fluid to be treated, with the fluid moving from the influent point, flowing vertically toward the UV light source, and then exits the effluent point. The at least one UV light source is positioned above the fluid to be treated and projecting UV light rays downward toward and into the fluid to be treated, with the fluid moving upward toward the UV light source. Several UV dose zones are established within the system. The first zone is the light source system exit UV dose zone, which occurs at the light source system and air interface. Then next zone is the air UV dose zone which occurs just beneath the UV light source and just above the water and the at least one interface plate. The next zone is the interface plate UV dose zone, which occurs at the intersection of the water and the at least one interface plate. The at least one interface plate is used to provide a surface zone for UV disinfection above the fluid and to provide additional treatment means for balancing pH, affecting effluent chemistry, providing a catalyst, and the like. The last zone is the submerged UV dose zone, which creates a variable UV dose zone that decreases in effectiveness at greater distances from the UV light source. Commercial-scale applications for buildings or multi-family dwellings are constructed similarly, only using a plurality of vertical riser units, as necessary for the water flow requirements of that facility. Thus, a variety of features that have lead to a significant improvement to the design of a UV disinfection system are shown, allowing simplified, lower cost facilities, higher water processing rates, and an ultimately superior product.

An alternative embodiment of the present invention is connected to a fluid reservoir. The first aspect of the reservoir system is a fluid reservoir. In this system, the UV light source is positioned within a UV light source system, including optical components, above the fluid stored in the reservoir and projecting a UV dose zone downward toward and into the fluid to be pre-treated. This reservoir fluid could be previously treated/purified or not. The at least one UV light source is positioned above the fluid to be treated and projecting UV light rays downward toward and into the fluid to be pre-treated. The light source system is provided in the reservoir system to prevent microorganism build-up in the reservoir. For completion of the system, a single vertical riser UV light source system is constructed and configured to be attached to the reservoir system. In this system, the UV light source is positioned within a UV light source system, including optical components (not shown), above the fluid to be treated and projecting a UV dose zone downward toward and into the fluid to be treated, with the fluid moving from the influent point (reservoir effluent point), flowing vertically toward the UV light source, and then exits the effluent point. The at least one UV light source is positioned above the fluid to be treated and projecting UV light rays downward toward and into the fluid to be treated, with the fluid moving upward toward the UV light source. Several UV dose zones are established within the system. The first zone is the light source system exit UV dose zone, which occurs at the light source system and air interface. Then next zone is the air UV dose zone which occurs just beneath the UV light source and just above the water and the at least one interface plate. The next zone is the interface plate UV dose zone which occurs at the intersection of the water and the at least one interface plate. The at least one interface plate is used to provide a surface zone for UV disinfection above the fluid and to provide additional treatment means for balancing pH, affecting effluent chemistry, providing a catalyst, and the like. The last zone is the submerged UV dose zone, which creates a variable UV dose zone that decreases in effectiveness at greater distances from the UV light source.

The foregoing described the general features of selected UV water disinfection system applications, including wastewater treatment, other water purification, e.g., drinking water, and the like, for permanent or fixed-system installations and configurations. However, the present invention is also useful for application in a portable water disinfection system.

The following provides an alternate embodiment that includes selected desirable features of the present invention. There are a number of very high power tubular lamps that may be employed in another embodiment for UV light source system and hydraulic system combinations. The medium pressure lamps could be used, albeit at a much higher power level that was indicated for the commercially available Trojan Tech design (300 W). Medium pressure lamps are available in the multi-kiloWatt range. The high power lamps, e.g., Vortek lamps, are a desirable source since they have strong UV emission, and are available in the 100's of kW to MegaWatt range.

In one embodiment, the water flow is in a horizontal channel or direction, which does not require all of the vertical riser components, like the interface plate and some hydraulic components. However, optical components are desirably included in the planar or horizontal (also referred to as retrofit) designs. The water turbulence could be achieved by having horizontal "foils" (like those on the trailing edge of an airplane wind), immersed in the flow channel. These foils would make a shallow turbulent region in the flow channel allowing good exposure of the infected water past the lamps. In this simple way, the function of the complex vertical riser would be achieved, with much fewer parts.

Thus the configuration includes a number of cylindrical or tubular light sources or lamps oriented and arranged in a horizontally spaced-apart distance from each other in a non-submerged configuration over a flowing fluid stream, with each lamp having a foil positioned approximately directly under it to provide the turbulent flow mixing desired.

The fundamental physical parameters that control the design for these compact/short arc kinds of systems according to the present invention include: the lamp power per unit length [P]; the Cylindrical Riser flow tube Cross-section[A]; the dosing required [D] where D=Energy/volume, and the flow rate & dwell time. For the purposes of this analysis the cell widths are between about 10 cm and about 15 cm, the water penetration approximately about 10 cm. The dwell time depends on the effectiveness of the turbulent mixing, the influent characteristics, and type of contamination.

A cylindrical riser for cell of 10 to 15 cm diameter as being a practical size, thereby providing a disinfection dosage, D=Energy/volume=E/V which varies from about 50 J/liter to perhaps 500 J/liter.

The three parameters T, P/A, and D control the possible/practical flow geometries. Since P/V=E/V/T where P=input power, E=input energy, V=volume of water being processed & T=dwell time, then P/[A*d]=D/T where D=E/V, the input energy/volume, or dosing Then, T=D*d/[P/A]

T=D(J/liter)*d(cm)*(1 liter/1000 cm^3)/[P/A(W/cm^2)].

Further, P/A=P/[pi*dia*dia/4]~3000/[3.14*10*10/4]~38 W/cm^2 for 3000 W Hg, & a 4" diameter vertical riser configuration.

P/A~20000/[3.14*15*15/4]~113 W/cm^2 for Xe & a 6" dia riser

TABLE 1

Dwell Time for Compact/Short-arc Mercury and Xenon Lamps

| Lamp type V | Wattage | Dose (J/I) | | | |
|---|---|---|---|---|---|
| | | 50 | 100 | 200 | 500 |
| Mercury 40 W/cm^2 | 40 | 0.013 | 0.025 | 0.050 | 0.125 |
| Xenon 100 W/cm^2 | 100 | 0.005 | 0.010 | 0.020 | 0.050 |

Surprisingly and significantly, these dwell times are much shorter than understood or set forth and commonly accepted and used within prior art. If the lamp power is reduced to 10%, and increase the cell diameter 2x, the results of Table 2 exist (SEE BELOW).

P/A=P/[pi*dia*dia/4]~300/[3.14*15*15/4]~1 W/cm^2 for 300 W Hg, & a 6-inch diam. riser; also P/A~2000/[3.14*30*30/4]~2.8 W/cm^2 for Xe & a 12-inch diam. riser

TABLE 2

Dwell Time for Compact/Short-arc Mercury & Xenon Lamps

| Lamp type V | Wattage | Dose (J/I) | | | |
|---|---|---|---|---|---|
| | | 50 | 100 | 200 | 500 |
| Mercury 1 W/cm^2 | 1 | 0.500 | 1.000 | 2.000 | 5.000 |
| Xenon 2.5 W/cm^2 | 2.5 | 0.200 | 0.400 | 0.800 | 2.000 |

Note that the dwell times are up to about a second if the irradiance is reduced by about a factor of 40, for example by reducing the lamp power to 10%, and increasing the cell diameter by x2 to 8" and 12" respectively. These are fairly large cells with low power lamps, so it would take a lot of these to process very much water per day, making their economic practicality more questionable.

For high power density processing cells, the dwell time is much shorter than the between about 6-second to about 10-second dwell time indicated in the foregoing. In order to get dwell times of between about 6 seconds to about 10 seconds, the lamp power must be less than 10% of the kilowatt levels selected or predetermined, and the cell diameters must be correspondingly much larger, e.g., up to 3x larger diameter. Those numbers would not be very consistent with the geometry of the short/compact arc lamp cylindrical risers; as such, the range of possible and feasible configurations for the system according to the present invention is flexible to accommodate a variety of lamp types and powers.

A main factor for consideration with respect to arc lamp spectra is the percentage of UV light output found in approximately the disinfection wavelength region, namely UVB&C from between about 200 to about 300 nm. The UV light sources contemplated within the scope of the present invention indicate that the peak of the disinfection effect occurs at about 265 nm. Also, the UV light available for disinfection effect is reduced gradually on the short wavelength side, and rapidly on the long wavelength side.

Notably, low-pressure mercury (Hg) arc lamps are efficient radiators in the UVB&C bands due to a resonant emission at about 254 nm. Advantageously, this is close to the optimum UVC wavelength for disinfection of the fluid. Generally, the total emission of radiation by a low-pressure tubular, germicidal lamp is about 20 to 35%, depending on the design and operating parameters (the rest of the power being consumed to heat the electrodes and the bulb) with 80 to 90% in about the 254 nm wavelength. Thus, UVC efficacy is about 20 to 30%. The other principle line is at 365 nm, which is outside the disinfection range. In some bulb designs it is the 365 nm line that dominates, and the disinfection effect will be substantially reduced.

At low pressure, the plasma that forms the arc is in the "glow regime," which is characterized by high electron temperatures, and much lower ion and neutral gas temperatures (typically Te~10,000 K, Ti~Tg~500 K). Under these conditions, the plasma is optically transparent, and a few, very narrow emission "lines" characterize the spectrum. Here, the emissivity will be low <0.1.

As the plasma temperature and density is increased (requiring higher current), the arc temperature increases.

The plasma becomes optically thick, and the electron, ion and neutral gas temperature become comparable. The spectrum becomes characterized by a blackbody continuum with a few lines superposed on it. A rule of quantum physics is that the peak of the lines must be below the blackbody curve for that temperature, so a blackbody curve can be fit to the peaks of the lines to deduce the effective arc temperature, but the bulk of the emission will be from the continuum under the lines.

As an example, consider the high pressure Argon, commercially available Vortek lamp. This lamp is a high pressure Argon arc operated at very high loading (Pin/L). To be specific, consider the 100 kW lamp. The length is 20 cm, so the loading is 5 kW/cm. The radiated output is given as 40 kW, 2 kW/cm so the efficiency is 40% (other Vortek lamps are up to, and perhaps exceeding 50% radiative efficiency. The spectrum indicates a peak at 800 nm which corresponds to an arc temperature deduced from Wien's law (2898 K/Wmax(um))=T(K)) of ~3600 K (the quoted figure is 3800 K). Calculating the blackbody emission from the arc with diameter 1.1 cm at 3800 K, the result gives 1.8 kW/cm with emissivity of 0.4.

The UVB&C emission of the Vortek 100 kW lamp rises almost linearly from 200 to 300 nm. Thus, the UVB&C efficacy is about 5%, and the UVB&C emission is about 5 kW. Notably, this is near the blackbody limit for a higher temperature (6500 K). The low emissivity occurs through the visible and NIR spectrum. Additionally, the lamps emit about 5% UVB&C-200 to 300 nm, 10% UVA300–400 nm, 30% visible-400 to 700 nm, and 50% NIR at 700 to 1400 nm). However, the results are affected by arc temperature; the results set forth herein are associated with low arc temperature. As the arc temperature is increased, the amount of UVB&C increases dramatically, e.g., if the arc temperature is increased to 8600 K, the UVB&C efficacy increases to 20%, which is comparable to the germicidal lamps.

Figure 1B:
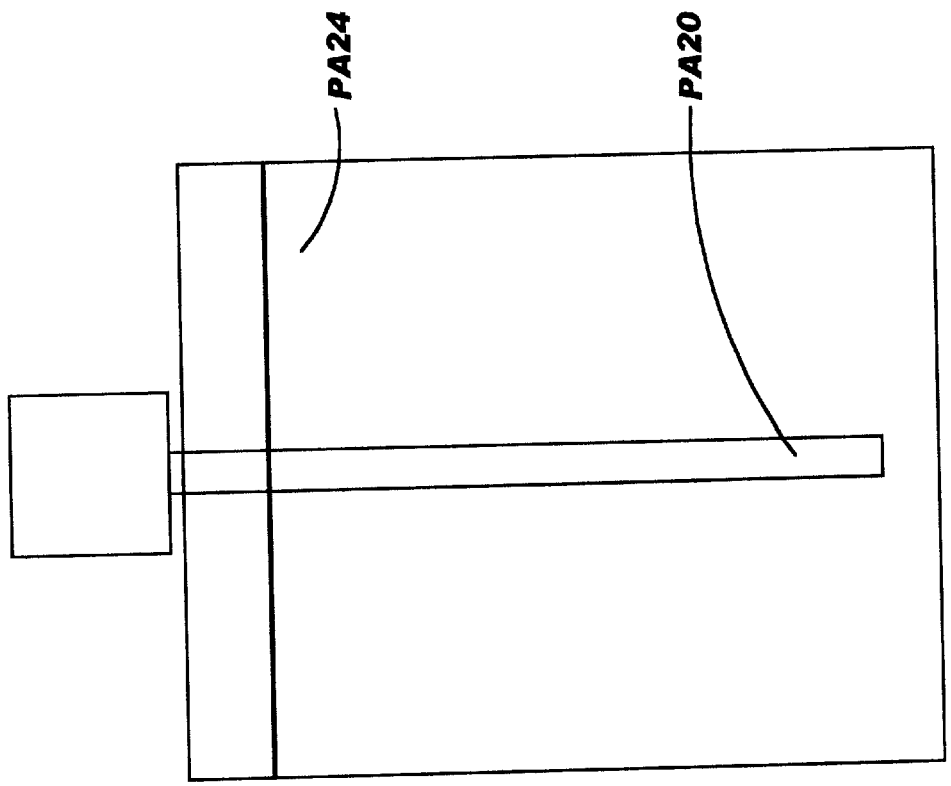

Notably, the UV content in these lamps is much higher in comparison to that of the Vortek lamp. Vortek estimate is T~3800 K and about 1.5% in UVB&C, while the lamp of FIG. 1b is T~8000 K about 9% in UVB&C. Assuming an overall efficiency of 50%, the result is about 5% UVB&C efficiency.

The following analysis relates to a high-pressure xenon (Xe) lamp. For a 20 kW xenon short arc, the peak blackbody emission is about 660 nm and corresponding to a temperature of about 4500 K. The spectrum is quasi-blackbody, with an estimated emissivity of between about 60 to about 80%. The UVB&C emission of this lamp is about 3% of the total but appears to have a glass cut off at about 240 nm; as such, the emissivity may be higher, about 6%. For a total emission efficiency of 70%, the corresponding UVB&C is between about 2% to about 4%.

The following analysis is associated with a high-pressure mercury (Hg) lamp, wherein a short-arc lamp appears to be fairly low pressure as characterized by a line spectrum. The spectrum representative of a high pressure Hg lamp notably includes a predominant line at about 254 nm, which is in the well-established UVB&C disinfection range. Most of the UV appears in the UVA range 300 to 400 nm, which is not useful according to the prior art systems; surprisingly, this high-pressure lamp is effective when used in the preferred embodiments according to the present invention. However, the spectrum is more difficult to quantify than those of lamps set forth in the foregoing, with an apparent temperature of about 8000 K and an emissivity of approximately about 0.1.

Generally, the high pressure lamps will have lower UVB&C efficacy than the low pressure germicidal lamps, but due to the higher power rating will have much more total UVB&C emission.

Additionally, there exists a commercially available High Power Lamp (HPL) in this long cylindrical form, made by Fusion Systems, and driven by a RF power source (rather than DC as most of the rest) that also works effectively with the UV fluid disinfection system and method according to the present invention. The discharge of this HPL is electrodeless, and the lamp life is good, approximately 5000 hours. These tubular lamps are most consistent with axial flow systems and retrofit design configurations for embodiments of the present invention, or Planar Vertical Riser (PVR) systems. The parameters for the Compact/Short-arc Lamps (CSL) and Cylindrical Vertical Riser (CVR) are consistent with the calculations and examples set forth herein.

The fundamental physical parameters that control the design for these kinds of systems are the lamp power per unit length, P/L, the dosing required, D=Energy/volume, and the flow rate & dwell time. Considering the dwell time to be T=about 1 to about 100 seconds, the water penetration to be about 10 cm, which gives a flow velocity of about 1 cm/s for about 10 second dwell. The dwell time depends on the effectiveness of the turbulent mixing, effluent characteristics, and type of contamination.

The LPL, MPL, HPL, and UHPLs generally have the following characteristics:

| TUBULAR LAMP CHARACTERISTICS | | | |
| --- | --- | --- | --- |
| Lamp type | Power | Length | Power/length |
| LPL | <300 W | ~50 cm | <3 W/cm |
| MPL | 300 to 3000 W | ~100 cm | 3 to 30 W/cm |
| HPL | 2000 to 6000 W | ~25 cm | 240 W/cm |
| UHPL | 50 kW to 1000 kW | ~40 cm | 1 to 3 kW/cm |

Nominal values are used for these calculations, realizing that the lamp power/length can be adjusted by the pressure, current (input power), and the like. Because of the large difference in power/length (P/L), these lamps are suitable to be used in very different geometries and are considered to be within the scope and contemplation of various embodiments constructed, set forth, and taught consistent with and according to the present invention.

Assuming a lamp length of between about 25 cm to about 100 cm, a range of practical sizes, (note that for tubular lamps the minimum is approximately about 15 cm with a maximum approximately about 150 cm). Furthermore, since the lamp arc diameter is in the range of between about 3 cm to about 6 cm, the flow cell width is sized to be about that wide or wider. Significantly smaller widths require impractical amounts of lamp transverse image demagnification, whereby demagnification in the longitudinal axis is probably impractical. Thus, practical cell cross-sectional areas are about at least a few hundred square centimeters, and the corresponding widths at least about 10 cm or wider. At this point, it is assumed that the upper limit is to the flow cell width, approximately a few meters.

The disinfection dosage, D=Energy/volume=E/V varies from between about 50 J/liter to about 500 J/liter. The three parameters T, P/L, and D control the possible and/or practical flow geometries according to the following equation:

$(P/L)/w/d = E/V/T = D/T$

Correspondingly, the flow channel width [w] is set forth as follows:

$w = (P/L) * T/(D*d) = (P/L) * T/(D*d)$ $w = [P/L(W/cm) * T(sec)]/[D(J/l) * d(cm)] * [1000\ cm^3/liter]$ Analysis for the case for a 10-second water dwell (flow velocity ~1 cm/s) in the irradiated volume follows.

For selected four lamp types and selected four water quality levels, the results are approximately:

TABLE 3

FLOW CELL WIDTH FOR VARIOUS TYPES OF WATER
10 SECOND DWELL
AND LAMPS TYPES
(cm)

| Lamp type V | Dose (J/l) | | | | |
|---|---|---|---|---|---|
| | 50 | 100 | 200 | 500 | 1000 |
| LPL 2 W/cm | 40 | 20 | 10 | 4 | 2 |
| MPL 20 W/Cm | 400 | 200 | 100 | 40 | 20 |
| HPL 200 W/Cm | 4000 | 2000 | 1000 | 400 | 200 |
| UHPL 2000 W/cm | 40000 | 20000 | 10000 | 4000 | 2000 |

For the LPL, the cell widths are reasonable, except perhaps for the highest dosage water. So a single LPL could be used for water treatment with a reasonable flow cell width as long as the water is reasonable pure. The LPL systems that have been deployed, the dosage is always under 100 J/l, so these lamps should be appropriate for small flow cells and low volumetric flow rates unless many of them are used. One way to get higher P/L for higher dosage water using LPLs is to use more lamps per cell. The use of a few lamps oriented in a half star pattern would allow these low P/L lamps to treat more water in a larger cell. Another way to use LPLs with the higher dosage water would be to reduce the flow velocity (increase the dwell time, see Table 3).

For the MPL the cell widths are larger, allowing higher volumetric flow rates. For example, a 200 J/l system with a 20 W/cm lamp would have a 2 kW lamp, and cell length and width of 100 cm. The MPL seems to be suitable for most water types at 10-second dwell, except that the cells become a bit too large for the lowest dosage water. In that case, the flow speed could be increased (decrease the dwell time, see Table 5)

The HPL (Fusion Lamp) has more than enough power to treat a system with a 10-second dwell time, and is more suited to shorter dwell time processing (see Table 5). The UHPL is not suitable with a planar vertical riser design with 10-second dwell, and more suitable for a freely flowing configuration, or much shorter dwell times. Thus, within some limits, both the LPL and MPL could be used with 10-second dwell for a Planar Vertical Riser System, a preferred embodiment according to the present invention.

Where the dwell time is decreased to about 1 second, then the cross section could be decreased by a factor of 10, and the flow velocity is correspondingly increased by the same factor. Table 4 (below) shows these results for 1-second dwell (~10 cm/s flow velocity):

TABLE 4

FLOW CELL WIDTH FOR VARIOUS TYPES OF WATER
1 SECOND DWELL
AND LAMPS TYPES
(cm)

| Lamp type V | Dose (J/l) | | | | |
|---|---|---|---|---|---|
| | 50 | 100 | 200 | 500 | 1000 |
| LPL 2 W/cm | 4 | 2 | 1 | 0.4 | 2 |
| MPL 20 W/cm | 40 | 20 | 10 | 4 | 20 |
| HPL 200 W/cm | 400 | 200 | 100 | 40 | 200 |
| UHPL 2000 W/cm | 4000 | 20000 | 1000 | 400 | 2000 |

The cell widths for LPL are too small, as is true for the MPLs width for the highest dosage water. A MPL system is particularly effective for the lower dose water, and for the higher dose water by using a few of the medium power lamps, and a somewhat wider cell. The HPL is now well suited to the flow channel size, except for the lowest dose water, where the dwell time would need to be reduced even further. The UHPL is appropriately used for large flow cells, provided that the dwell time is reduced respectively. For the highest dose water, the flow cells are of a practical size to work with a vertical riser system as shown in FIG. 2, provided the light is allowed to diverge considerably, and subsecond dwell times are permissible, such as at the interface plate and associated UV dose zone.

As another illustration, consider the flow cell sizes for longer dwell water processing shown in Table 5.

TABLE 5

FLOW CELL WIDTH FOR VARIOUS TYPES OF WATER
100 SECOND DWELL
AND LAMPS TYPES
(cm)

| Lamp type V | Dose (J/l) | | | | |
|---|---|---|---|---|---|
| | 50 | 100 | 200 | 500 | 1000 |
| LPL 2 W/cm | 400 | 200 | 100 | 40 | 2 |
| MPL 20 W/cm | 4000 | 2000 | 1000 | 400 | 20 |
| HPL 200 W/cm | 40000 | 20000 | 10000 | 4000 | 200 |
| UHPL 2000 W/cm | 400000 | 200000 | 100000 | 40000 | 2000 |

With a 100 second dwell, the cell widths for all the higher power types of lamps arc not necessarily the most practical design selection, although still functional As the dwell time changes, the flexibility of system configuration according to the present invention permits that various tubular lamps can be used to process differing water types or fluids having various characteristics with reasonable flow cell cross-sections. The UHPLs can process all 4 water types (from between about 50 J/l to about 500 J/l) and at dwell time less than 1 second, as appropriate for a given fluid treatment system. HPLs can process water at dwell times around 1 second. MPLs can be used to process water with between about 1 to a bout 10-second dwell, with the longer dwell time being used for highest dosage and the shorter dwell time used for the lower dosage water. Additionally, LPLs are capable of processing the lower dosage water with about 10 second dwell and the higher dosage water with a 100 second dwell. A germicidal lamp system can be used for the longer dwell times, where the flow cell cross-section becomes small requiring different optical demagnification.

The following section sets forth selected particular design examples for particular water processing applications.

DESIGN EXAMPLES

This section outlines a few design examples, not necessarily optimized, but illustrative of what can be done for a UV fluid disinfection system and method, wherein the fluid is water. These design examples include:

- Laboratory effluent purifier
- Home effluent purifier
- Housing complex effluent purifier
- Township effluent purifier
- City effluent purifier
- Large city effluent purifier
- Megalopolis effluent purifier

Laboratory Effluent Purifier (Small Mercury Lamp)

Mercury Lamp power <150 W, ~30,000 gallons per day (gpd). Flow cell is about 100 cm long by about 10 cm diameter.

The goal for this embodiment is to produce biologically disinfected water for discharge into the municipal sewage system. The fluid is diluted to an acceptable level by a turbidity dilution system. The UV dose required for disinfection of the water is low, below about 100 J/l. One compact arc mercury lamp is used with a small cell, approximately about 10 cm diameter by about 100 cm long with a maximum power of a few hundred Watts. The water dwell time is about one second.

Home Effluent Purifier (1 Mercury Lamp)

Mercury Lamp power is less than about 150 W, approximately about 3000 gpd. Flow cell is about 100 cm long by approximately about 10 cm diameter. In this case, it is assumed that the effluent provided is previously treated sewage. It would be particularly appropriate for homes that have independent water treatment facilities that discharge into the local environment, such as coastal regions, remote locations, or resorts, or similar localities. Assuming at least about 100 J/l are needed, but that less than 500 J/l will be adequate for this type of system. The dwell time is about 100 seconds. The system is designed to function on demand, capable of purifying effluent from a large household using a small compact arc lamp, used in a configuration having a function similar to that shown in FIG. 5. Since a single lamp is used, a monitoring system or control system is desirable to provide an indication when the lamp needs to be replaced or when other service to the system is needed or suggested.

Since the water demand is relatively low and the cell water flow rate is relatively high by comparison, the dwell could be increased whereby the lamp operates part of the time or intermittently, either by sensing control or by timer. This intermittent-type system arrangement beneficially extends the lamp life thereby providing a longer replacement time or lamp life cycle. Since the lamp life is degraded by turning it off and on, the system can be constructed and configured to allow the reservoir to be significantly depleted before restarting the lamp (e.g., where a sewage reservoir or tank is used, the lamp activity can be controlled, preprogrammed, and otherwise regulated to correspond to the tank water size and water level. Depending on the size of the reservoir, and the number of people using the system (as measured in discharged or used gallons/day), the lamp is arranged, configured, and programmed to run intermittently, e.g., for an hour or so per day. In this way, a lamp continuous operation life of about a month could be extended to perhaps a year, depending upon the particular characteristics and specifications of the system, including water characteristics.

Housing Complex Effluent Purifier (Multiple Mercury Lamps)

Mercury Lamp power approximately about 3 kW with approximately about 30,000 gpd. Six (6) Lamps at about 500 W, Flow cell about 100 cm long by about 20 cm diameter. This design would be similar to the Home water purifier set forth in the foregoing, except that it would use multiple lamps to accommodate the increased effluent and use and to ensure operation in the event of a lamp failure. In this embodiment, the lamps are constructed and controlled to run all of the time, and be replaced on a regular maintenance schedule, e.g., weekly or monthly. If one lamp were to fail, that flow tube is closed via an automatic lamp status detection system and control system. Approximate dwell time associated with a typical configuration for this example is about a minute.

Township Water Effluent Purifier (Dozens of Mercury Lamps)

Mercury lamp power approximately about 12 kW, including about a dozen 1 kW lamps, approximately about 300,000 gpd. This system includes a small number of units similar the previous housing complex unit, or a smaller number of larger units. This system is capable of purifying the discharge water for a small town of a few thousand people, using a few dozen small mercury lamps or a few higher power lamps, depending upon system characteristics and specifications.

City Water Effluent Purifier (100's of Mercury Lamps or Perhaps a Smaller Number of Xenon Lamps)

Mercury lamp power approximately about 1 MW, or Xenon lamp power approximately about 1 MW, about 10 Mgpd. This example could effectively be supported by about 300 each of 3 kW lamps, and each cell being about 100 cm long. There are two different approaches to the UV disinfectant system for this example: (1) to increase the number of Mercury lamps as in the previous examples (it would take 100's of C/S HPLs), or (2) to use less than about ⅓ as many Xenon lamps. Since the Xenon lamp is an adequately efficient generator of IUVB&C, it would simplify the construction and maintenance of the system.

Large City Effluent Purifier (Thousand of Mercury, or Perhaps a Few Hundred Xenon Lamps)

MPL lamp power approximately about 3 MW, approximately about 30 Mgpd. This example is merely a scale-up of the previous water treatment systems. Clearly, the advantage of the UHPLs is more apparent as scale increases.

Megalopolis Effluent Purifier (Few Thousand Mercury Lamps)

MPL lamp power approximately about 10 MW, about 100+ Mgpd. Continuing the scale-up to a capacity for 1 million people. This is comparable to commercial applications of the prior art larger Trojan Tech system, except that the present invention advantageously uses much fewer, higher power Compact/Short arc Lamps, and in a non-submerged configuration thereby providing more effective UV dosing with less maintenance and increased efficiency and effectiveness of the overall system.

For cylindrical flow cell configurations and consideration of specific scales of applications for water purification systems using the UV disinfection system and method according to the present invention, several scenarios are presented as follows by way of estimation and illustration of the distinction and differences between the present invention and prior art; the figures are not intended to be self-limiting for practical application precision, but are used to facilitate understanding of the present invention and its preferred embodiments.

For laboratory effluent purifier use: 1 mercury C/S HPL. A practical design is achieved using one <300 W High Pressure Compact/Short-arc Lamp or a few smaller lamps (C/S HPLs). The flow cell is about 100 cm long by less than about 2.5 cm diameter, the dwell time between about 16 seconds to about 33 seconds. For a home effluent purifier: 1 mercury C/S HPL. A home effluent purifier based on one low power <30 WC/S HPL is feasible. A cell about 100 cm long by about 2.5 cm wide works well. The dwell time is approximately less than 167 seconds. For a housing complex effluent purifier: 6 C/S HPLs; a system with six 500 W C/S HPL is capable of purifying effluent for a condo or apartment complex. The flow cell is about the same size as the home effluent purifier, but the use of a plurality of lamps and vertical risers increases the flow volume, giving the system more demand capacity. For a township effluent purifier: about a dozen MPLs and flow cells are required to ensure disinfection at reasonable flow rates. In this type of case and scale, a system based six 2 kW C/S HPLs or a larger number of smaller lamps is effective. For a standard city effluent purifier: hundreds of C/S HPL, or a smaller number of Xenon lamps, are used with the system and method according to the present invention. A system based on a hundred C/S HPLs or a smaller number of xenon lamps works to provide efficient and effective fluid disinfection by UV dosage and exposure. For a large city effluent purifier: approximately about 1000 C/S HPLs (mercury). A system based on thousands of MPLs or a few dozen UHPLs also works effectively. For a megalopolis effluent purifier: thousands of C/S HPLs are required. Significantly, since for this scale of application, thousands of C/S HPLS are needed, the benefits of using higher power lamps becomes even stronger, and particularly effective using the configurations of the UV fluid disinfection system and method according to the present invention.

The use of Compact/Short-arc High Pressure Lamps and Cylindrical Vertical Risers creates a more complex system than using Medium Pressure Lamps and Planar Vertical Risers, due to the need for more lamp power, which is due to lower UVB&C efficacy, and more complex riser geometry. However, the use of higher power xenon lamps, depending on their somewhat uncertain UVB&C efficacy, reduces the number of lamps required, depending on the fluid characteristics and flow rates desired. Thus, the UV disinfectant system according to the present invention provides efficient and effective treatment of fluid, particularly water in wastewater treatment and other industrial applications.

The present invention requires some pretreatment of the wastewater in cases of wastewater with high turbidity prior to exposure to UV dose zones of the present invention. Traditional means for reducing turbidity including, but not limited to, filtration, dilution, reverse osmosis and chemical treatment may be advantageously employed to increase the UV efficacy of the system according to the present invention. However, certain aspects of the preferred embodiment allow it to more easily handle high turbidity fluids than the prior art.

The interface plate may induce turbulence or cause fluid cascade with a non-planar surface, stair-step surface, downwardly sloping surface, or other the like. The induction of turbulence is particularly advantageous when the fluid is turbid. Turbidity, which is the state of water when it is cloudy from having sediment stirred up, interferes with the transmission of UV energy and decreases the disinfection efficiency of the UV light disinfection system. Thus, turbulence, by inducing rotation in the particle, causes all aspects of a particle to be exposed to the UV light. Additionally, the photocatalytic properties of the system reduce turbidity by degrading the compounds or particles responsible for the turbidity. Furthermore, the reflective aspects of the surfaces of the system enhance the efficacy of the system when operated under turbid conditions because the UV light can strike the various aspects of a particle with the need for the particle to be rotating, thus overcoming the opacity of the particle. Another aspect that enhances performance under turbid conditions is the high UV light intensity of the system. The high UV light intensity can more easily compensate for fluctuations in turbidity than lower-intensity systems. Thus, the preferred embodiment has several characteristics that enhance its performance under turbid conditions.

In cases where the water has high iron or manganese content, is clouded and/or has organic impurities, it is usually necessary to pre-treat the water before it enters the UV disinfection stage because deposits on the quartz-encased submerged UV lamps, which are immersed in the water to be treated, interfere with the UV light transmission, thereby reducing the UV dose and rendering the system ineffective. Prior art typically employs UV purification in conjunction with carbon filtration, reverse osmosis and with certain chemicals to reduce fouling between cleanings of the quartz sleeves that surround the UV lamps. Thus, another advantage of the preferred embodiment is that turbidity reduction is not necessary for the system to perform adequately, and thus the system eliminates the need for expensive pre-treatment of the fluid to reduce turbidity.

The contribution of the reflectance of internal surfaces to the efficacy of the system can be capitalized upon by incorporating UV-reflective materials and reflection-enhance design into the reservoir. These same surfaces can also be manufactured such that they incorporate photocatalysts, as previously taught for the interface plate. Moreover, additional surfaces to support photocatalyst may be added to the reservoir or VRC system. Thus, an integrated design that incorporates UV-reflectant materials, UV-reflectant design, photocatalysts, and additional photocatalyst surfaces will greatly enhance the efficacy of the system.

Certain modifications and improvements will occur to those skilled in the art upon a reading of the foregoing description. By way of example, various optical components are used depending upon the particular UV light source or lamp selection for a given system. Also, a plurality of UV light source systems, either planar horizontal or retrofit configurations and/or cylindrical vertical riser configurations, may be combined and arranged in series to increase the flow rates for which effective UV disinfection of the fluid occurs. Moreover, a wide range of fluid applications are contemplated within the scope of the present invention, including application of the UV fluid disinfectant system and method to wastewater, commercial and industrial wastewater, agricultural sludge and other waste and wastewater, biomedical and bodily fluids, fluid contaminants influents, and effluents, and the like are contemplated applications for the present invention, without substantial departure from the embodiments and teachings contained within this specification. Additionally, surface treatment, including non-planar surfaces, for UV disinfection of microorganisms thereon are contemplated applications properly considered within the scope of the present invention. All modifications and improvements have been deleted herein for the sake of conciseness and readability but are properly within the scope of the following claims.

I claim:

1. An ultraviolet disinfection (UV) system for treating waste-containing fluid, the system comprising at least one light source positioned within a housing and connected to a power source for producing a UV light output from the housing, the system including at least one optical component positioned between the at least one light source and the UV light output from the housing, thereby producing a focused, controllable UV light output that has at least one UV dose zone for providing effective sterilization of microorganisms within the fluid.

2. The UV system according to claim 1, wherein the at least one UV light source is one lamp.

3. The UV system according to claim 1, wherein the at least one UV light source is a UV lamp.

4. The UV system according to claim 3, wherein the at least one UV light source is a spectral calibration lamp.

5. The UV system according to claim 3, wherein the at least one UV light source is an electrodeless lamp.

6. The UV system according to claim 3, wherein the at least one UV light source is a mercury halide lamp.

7. The UV system according to claim 1, wherein the at least one UV light source is a light pump device.

8. The UV system according to claim 7, wherein the output from the at least one UV light source is distributed by fiber optic transmission lines.

9. The UV system according to claim 7, wherein the fiber optic transmission lines having a first end connected to the housing output such that the UV light output from the housing passes through the fiber optic transmission lines and exiting from a second end such that the UV light output exiting the fiber optic transmission lines is projected into the fluid.

10. The UV system according to claim 8, wherein the fiberoptic lines include acrylic fibers.

11. The UV system according to claim 8, wherein the fiberoptic lines include glass fibers.

12. The UV system according to claim 8, wherein the fiberoptic lines include liquid core fibers.

13. The UV system according to claim 8, wherein the fiberoptic lines include hollow core fibers.

14. The UV system according to claim 8, wherein the fibcroptic lines include core-sheath fibers.

15. The UV system according to claim 8, wherein at least one fluid-containing device is connected to the light pump device via fiberoptic transmission lines.

16. The UV system according to claim 1, further including a non-fouling lamp housing thereby eliminating cleaning of the lamp housing to ensure consistent UV disinfection of the fluid.

17. The UV system according to claim 1, wherein the light housing is affixed to a reservoir and the UV light output disinfects a substantially non-flowing water supply contained within the reservoir.

18. The UV system according to claim 17, wherein the system has a non-vertical riser configuration.

19. The UV system according to claim 1, wherein the lamp housing is affixed to a reservoir with flowing water contained therein.

20. The UV system according to claim 2, further including a vertical riser configuration (VRC) wherein the fluid is moved at a predetermined rate toward the UV light output thereby producing an increasing UV dose zone within the fluid as it approaches the light output.

21. The UV system according to claim 20, wherein an interface zone that is formed at the interface plate includes at least one additive that influence characteristics of the fluid as the fluid passes through the interface zone and over a surface zone that exists at a superior surface of the interface plate that is positioned closest to the UV light source.

22. The UV system according to claim 21, wherein the at least one additive is selected from the group consisting of TiO2, WO2, ZnO, ZnS, SnO2, and PtTiO2.

23. The UV system according to claim 20, wherein the vertical riser configuration system is portable.

24. The UV system according to claim 20, wherein the vertical riser configuration system is scalable to applications.

25. The UV system according to claim 20, wherein the system is adaptable to be removably connected to a piping system for carrying water to an end user output, such that a multiplicity of systems may be positioned to function at a corresponding multiplicity of end user outputs to provide disinfected, purified water in many locations at once.

26. The UV system according to claim 1, wherein the at least one optical component is selected from the group consisting of reflectors, shutters, lenses, splitters, focalizers, mirrors, rigid and flexible light guides, homogenizer, mixing rods, manifolds and other couplers, filters, gratings, diffracters, color wheels and fiber optic transmission lines.

27. The UV system according to claim 1, wherein at least one optical component is an off-axis optical component.

28. The UV system according to claim 1, wherein at least one optical component is a gradient component.

29. The UV system according to claim 1, wherein at least one optical component is UV transmissive.

30. The UV system according to claim 1, wherein at least one optical component is UV reflective.

31. The UV system according to claim 1 wherein the at least one optical component includes fiber optic transmission lines having a first end connected to the housing output such that the UV light output from the housing passes through the fiber optic transmission lines and exiting from a second end such that the UV light output exiting the fiber optic transmission lines is projected into the fluid.

32. The UV system according to claim 26, wherein the at least one optical component is a lens for focusing light from the light source through an output point in the housing and into the fluid for disinfection thereof.

33. The UV system according to claim 32, wherein the lens is a parabolic lens.

34. The UV system according to claim 1, wherein the at least one UV dose zone includes a water-air interface dose zone and a variable intra-fluid dose zone.

35. The UV system according to claim 1, wherein the at least one UV light source is positioned outside the fluid to be treated thereby providing effective sterilization of microorganisms within the fluid.

36. An ultraviolet disinfection (UV) system for treating waste-containing fluid, the system comprising at least one light source positioned outside the fluid to be treated and positioned within a housing and connected to a power source for producing a UV light output from the housing, the system including at least one optical component positioned between the at least one light source and the UV light output from the housing, thereby producing a focused, controllable UV light output that has at least one UV dose zone for providing effective sterilization of microorganisms within the fluid.

37. The UV system according to claim 36, wherein the at least one UV light source is a single UV lamp.

38. The UV system according to claim 36, wherein the at least one UV light source is a spectral calibration lamp.

39. The UV system according to claim 36, wherein the at least one UV light source is an electrodeless lamp.

40. The UV system according to claim 36, wherein the at least one UV light source is a mercury halide lamp.

41. The UV system according to claim 36, wherein the at least one UV light source is a light pump device.

42. The UV system according to claim 36, wherein the at least one UV light source is a pulsed lamp device.

43. The UV system according to claim 36, further including a non-fouling lamp housing thereby eliminating cleaning of the lamp housing to ensure consistent UV disinfection of the fluid.

44. The UV system according to claim 36, wherein the light housing is affixed to a reservoir and the UV light output disinfects a substantially non-flowing water supply contained within the reservoir.

45. The UV system according to claim 44, wherein the system has a non-vertical riser configuration.

46. The UV system according to claim 36, wherein the lamp housing is affixed to a reservoir with flowing water contained therein.

47. The UV system according to claim 36, further including a vertical riser configuration (VRC) wherein the fluid is moved at a predetermined rate toward the UV light output thereby producing an increasing UV dose zone within the fluid as it approaches the light output.

48. The UV system according to claim 36, wherein an interface zone that is formed at the interface plate includes at least one additive that influence characteristics of the water as the water passes through the interface zone and over a surface zone that exists at a superior surface of the interface plate that is positioned closest to the UV light source.

49. The UV system according to claim 48, wherein the at least one additive is selected from the group consisting of TiO2, WO2, ZnO, ZnS, SnO2, and PtTiO2.

50. The UV system according to claim 46, wherein the system is adaptable to be removably connected to a piping system for carrying water to an end user output, such that a multiplicity of systems may be positioned to function at a corresponding multiplicity of end user outputs to provide disinfected, purified water in many locations at once.

51. The UV system according to claim 36, wherein the at least one optical component is selected from the group consisting of reflectors, shutters, lenses, splitters, focalizers, mirrors, rigid and flexible light guides, homogenizer, mixing rods, manifolds and other couplers, filters, gratings, diffracters, color wheels and fiber optic transmission lines.

52. The UV system according to claim 36, wherein at least one optical component is UV transmissive.

53. The UV system according to claim 36, wherein at least one optical component is UV reflective.

54. The UV system according to claim 36, wherein the at least one optical component includes fiber optic transmission lines having a first end connected to the housing output such that the UV light output from the housing passes through the fiber optic transmission lines and exiting from a second end such that the UV light output exiting the fiber optic transmission lines is projected into the fluid.

55. The UV system according to claim 54, wherein the fiberoptic lines includeacrylic fibers.

56. The UV system according to claim 54, wherein the fiberoptic lines include glass fibers.

57. The UV system according to claim 54, wherein the fiberoptic lines include liquid core fibers.

58. The UV system according to claim 54, wherein the fiberoptic lines include hollow core fibers.

59. The UV system according to claim 54, wherein the fiberoptic lines include core-sheath fibers.

60. The UV system according to claim 51, wherein the at least one optical component is a lens for focusing light from the light source through an output point in the housing and into the fluid for disinfection thereof.

61. The UV system according to claim 60, wherein the lens is a parabolic lens.

62. The UV system according to claim 36, wherein the at least one UV dose zone includes a water-air interface dose zone and a variable intra-fluid dose zone.

63. A method for purifying waste-containing fluids comprising the steps of:
providing the fluid to be treated in a reservoir;
exposing the reservoir and fluid to a UV system comprising at least one light source positioned in a housing and connected to a power source for producing a UV light output from the housing, the system including at least one optical component positioned between the at least one light source and the UV light output from the housing;
producing a focused, controllable UV light output that has at least one UV dose zone for providing effective sterilization of microorganisms within the fluid.

64. The method according to claim 63, wherein the system includes a non-submerged light source.

65. A method for providing ultraviolet disinfection (UV) of waste-containing fluids, the method comprising the steps of
providing a UV disinfection system comprising at least one UV light source coupled with at least one UV-transmissive optical component outside a fluid to be treated and at least one interface zone positioned between the at least one UV light source and the fluid to be treated, the at least one UV light source designed, configured, and connected to produce UV light creating at least one UV dose zone outside the fluid;
presenting a surface zone on the at least one interface zone, wherein the surface zone has a UV dose zone associated therewith for disinfecting the fluid to be treated;
introducing a pre-treated fluid into the system, the fluid passing through at least one UV dose zone within the fluid and passing through the at least one interface zone and surface zone UV dose zone;
disinfecting the fluid via exposure to the UV light in the UV dose zones;
dispensing the disinfected fluid outside the system.

66. The method according to claim 65, further including the step of forcing water via a hydraulic system through a vertical riser configuration of the system.

67. The method according to claim 65, further including the step of modifying the fluid characteristics via at least one additive on the interface zone causing a reaction in the fluid.

68. The method according to claim 65, further including the step of introducing turbulence in the fluid as the fluid passes throughout the system, thereby increasing the exposure to UV light, disinfection, and catalytic chemical reactions.

69. The method according to claim 65, further including the step of introducing a catalyst at the interface zone.

* * * * *